(12) United States Patent
Slewinski

(10) Patent No.: US 12,421,521 B2
(45) Date of Patent: Sep. 23, 2025

(54) TRANSGENIC PLANTS WITH ENHANCED TRAITS

(71) Applicant: Monsanto Technology LLC, St. Louis, MO (US)

(72) Inventor: Thomas L. Slewinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 293 days.

(21) Appl. No.: 17/817,486

(22) Filed: Aug. 4, 2022

(65) Prior Publication Data

US 2023/0128674 A1    Apr. 27, 2023

Related U.S. Application Data

(62) Division of application No. 17/041,348, filed as application No. PCT/US2019/034196 on May 28, 2019, now abandoned.

(60) Provisional application No. 62/677,448, filed on May 29, 2018.

(51) Int. Cl.
  *C12N 15/82* (2006.01)
(52) U.S. Cl.
  CPC ................ *C12N 15/8213* (2013.01)
(58) Field of Classification Search
  None
  See application file for complete search history.

(56) References Cited

U.S. PATENT DOCUMENTS

| | | |
|---|---|---|
| 2006/0010515 A1 | 1/2006 | He |
| 2006/0150283 A1* | 7/2006 | Alexandrov et al. ......... C07K 14/415 536/23.6 |
| 2009/0183270 A1 | 7/2009 | Adams et al. |
| 2011/0016588 A1 | 1/2011 | He |
| 2012/0227131 A1 | 9/2012 | Abad et al. |
| 2012/0317677 A1 | 12/2012 | Andersen et al. |
| 2015/0113676 A1 | 4/2015 | Abad et al. |

FOREIGN PATENT DOCUMENTS

| | | |
|---|---|---|
| WO | 2004074442 | 9/2004 |
| WO | 2011120549 | 10/2011 |
| WO | 2015026886 | 2/2015 |
| WO | WO 2015/026886 A1 * | 2/2015 |
| WO | 2015154741 | 10/2015 |
| WO | 2016205703 A1 | 12/2016 |
| WO | 2017161063 | 9/2017 |
| WO | 2018054911 | 3/2018 |

OTHER PUBLICATIONS

Hill & Preiss (1998) Biochem Biophys Res Commun 244(2):573-77.*
Guo et al. (2004) Proc Natl Acad Sci USA 101:9205-10.*
Zhang (2003) Curr Opin Plant Biol 6:430-40.*
Wormit et al. (2006) Plant Cell 18:3476-90.*
Tittonell et al. (2005) Agric Ecosys Environ_105:213-220.*
International Search Report and Written Opinion for International Application No. PCT/US2019/034196 mailed Sep. 11, 2019.
European Office Action regarding European App. No. 19812313.5, dated Feb. 18, 2022.
Guo et al., Isopentenyl transferase gene (ipt) downstream transcriptionally fused with gene expression improves the growth of transgenic plants, Transgenic Research 19(2): 197-209, 2009.
Ma et al., "Expression of isopentenyl transferase gene (ipt) in leaf and stem delayed leaf senescence without affecting root growth", Plant Cell Reports 28(11): 1759-1765, 2009.
Hirose et al. (2017) GenBank AP018216.
GenBank Accession No. CAA90628.1, dated Aug. 17, 1996.
GenBank Accession No. ACU23290.1, dated Aug. 6, 2009.
GenBank Accession No. NP_176240.1, dated Feb. 14, 2019.
GenBank Accession No. BAA76344.1, dated Mar. 27, 1999.
GenBank Accession No. NP_053424.1, dated Dec. 16, 2014.
GenBank Accession No. NP_001146891.1, dated Dec. 29, 2017.
GenBank Accession No. CAB44641.1, dated Jul. 26, 2016.
GenBank Accession No. ACU19485.1, dated Aug. 6, 2009.
GenBank Accession No. AAD30608.1, dated Oct. 30, 2002.
GenBank Accession No. Q96450.1, dated Aug. 12, 2020.
De Frietas Lima, et al. Molecular mechanisms of biomass increase in plants, Biotechnology Research and Innovation 1:14-25, 2017.
Extended European Search Report regarding European Application No. 19812313.5, dated Jun. 14, 2022.
Shuai, Role and significance of sucrose-6-phosphate phosphatase in regulating sucrose biosynthesis and carbon partitioning in photosynthetic and non-photosynthetic tissue, Dissertation, available at http://www.biochmie.nat.uni-erlangen.de/files/Diss_Shuai_Chen.pdf, 2005.
Wang et al., Research advance of sucrose phosphate synthase (SPS) in higher plant, International Journal of Agriculture and Biology, 15:221-1226, 2013.

* cited by examiner

*Primary Examiner* — Russell T Boggs
(74) *Attorney, Agent, or Firm* — Dentons US LLP; Paula DeGrandis

(57) ABSTRACT

This disclosure provides recombinant DNA constructs and transgenic plants having enhanced traits such as increased yield, increased nitrogen use efficiency, and enhanced drought tolerance or water use efficiency. Transgenic plants may include field crops as well as plant propagules, plant parts and progeny of such transgenic plants. Methods of making and using such transgenic plants are also provided. This disclosure also provides methods of producing seed from such transgenic plants, growing such seed, and selecting progeny plants with enhanced traits. Also disclosed are transgenic plants with altered phenotypes which are useful for screening and selecting transgenic events for the desired enhanced trait.

26 Claims, No Drawings

Specification includes a Sequence Listing.

TRANSGENIC PLANTS WITH ENHANCED TRAITS

CROSS-REFERENCE TO RELATED APPLICATIONS

This application is a divisional of U.S. patent application Ser. No. 17/041,348, filed Sep. 24, 2020, which is a 371 National Stage application of International Application No. PCT/2019/034196, filed May 28, 2019, which claims the benefit of U.S. Provisional Application No. 62/677,448, filed May 29, 2018, each of which is incorporated herein by reference in its entirety.

INCORPORATION OF SEQUENCE LISTING

The sequence listing file named "MONS457USD1.xml", which is 65.4 kilobytes (measured in MS-WINDOWS) and was created on Aug. 3, 2022, is filed herewith and incorporated herein by reference in its entirety.

FIELD OF THE INVENTION

Disclosed herein are recombinant DNA constructs, plants having altered phenotypes, enhanced traits, increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with altered phenotypes, enhanced traits, increased yield, increased nitrogen use efficiency and increased water use efficiency.

SUMMARY

In one aspect, the present disclosure provides recombinant DNA constructs each comprising: (a) a polynucleotide sequence with at least 90%, at least 91%, at least 92%, at least 93%, at least 94%, at least 95%, at least 96%, at least 97%, at least 98%, at least 99%, or 100% identity to a sequence selected from the group consisting of SEQ ID NOs: 1-9; (b) a polynucleotide sequence that encodes a polypeptide comprising an amino acid sequence with at least 90%, at least 91%, at least 92%, at least 93%, at least 94%, at least 95%, at least 96%, at least 97%, at least 98%, at least 99%, or 100% identity to a sequence selected from the group consisting of SEQ ID NOs: 10-18 and 30-39.

Plants comprising a recombinant DNA construct may be a field crop plant, such as corn, soybean, cotton, canola, rice, barley, oat, wheat, turf grass, alfalfa, sugar beet, sunflower, *quinoa* and sugarcane. A plant comprising a recombinant DNA construct may have an altered phenotype or an enhanced trait as compared to a control plant. The enhanced trait may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. The altered phenotype may be, for example, plant height, biomass, canopy area, anthocyanin content, chlorophyll content, water applied, water content, and water use efficiency.

According to another aspect, the present disclosure provides methods for altering a phenotype, enhancing a trait, increasing yield, increasing nitrogen use efficiency, or increasing water use efficiency in a plant comprising producing a transgenic plant comprising a recombinant DNA construct of the present disclosure. The step of producing a transgenic plant may further comprise transforming a plant cell or tissue with the recombinant DNA construct, and regenerating or developing the transgenic plant from the plant cell or tissue comprising the recombinant DNA construct. The transgenic plant may then be crossed to (a) itself; (b) a second plant from the same plant line; (c) a wild type plant; or (d) a second plant from a different plant line, to produce one or more progeny plants; and a plant may be selected from the progeny plants having increased yield, increased nitrogen use efficiency, or increased water use efficiency, or other altered phenotype or enhanced trait as compared to a control plant. Plants produced by this method are further provided.

According to another aspect, the present disclosure provides recombinant DNA molecules for use as a donor template in site-directed integration, wherein a recombinant DNA molecule comprises an insertion sequence comprising: (a) a polynucleotide sequence with at least 90%, at least 91%, at least 92%, at least 93%, at least 94%, at least 95%, at least 96%, at least 97%, at least 98%, at least 99%, or 100% identity to a sequence selected from the group consisting of SEQ ID NOs: 1-9; (b) a polynucleotide sequence that encodes a polypeptide comprising an amino acid sequence with at least 90%, at least 91%, at least 92%, at least 93%, at least 94%, at least 95%, at least 96%, at least 97%, at least 98%, at least 99%, or 100% identity to a sequence selected from the group consisting of SEQ ID NOs:10-18 and 30-39.

The insertion sequence of a recombinant DNA molecule may comprise a heterologous promoter functional in a plant cell and operably linked to the polynucleotide sequence. The recombinant DNA molecule may further comprise at least one homology arm flanking the insertion sequence to direct the integration of the insertion sequence into a desired genomic locus. Plants, propagules and plant cells are further provided comprising the insertion sequence. According to some embodiments, the recombinant DNA molecule may further comprise an expression cassette encoding a site-specific nuclease and/or one or more guide RNAs.

According to another aspect, the present disclosure provides recombinant DNA molecules for use as a donor template in site-directed integration, wherein a recombinant DNA molecule comprises an insertion sequence for modulation of expression of an endogenous gene, wherein the endogenous gene comprises: (a) a polynucleotide sequence encoding a mRNA molecule with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs:1-9; or (b) a polynucleotide sequence that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 10-18 and 30-39.

The insertion sequence may comprise a promoter, an enhancer, an intron, or a terminator region, which may correspond to a promoter, an enhancer, an intron, or a terminator region of an endogenous gene. Plants, propagules and plant cells are further provided comprising the insertion sequence. The recombinant DNA molecule may further comprise at least one homology arm flanking the insertion sequence. According to some embodiments, the recombinant DNA molecule may further comprise an expression cassette encoding a site-specific nuclease and/or one or more guide RNAs.

According to another aspect, the present disclosure provides methods for altering a phenotype, enhancing a trait, increasing yield, increasing nitrogen use efficiency, or increasing water use efficiency in a plant comprising: (a) modifying the genome of a plant cell by: (i) identifying an endogenous gene of the plant corresponding to a gene selected from the list of genes in Tables 1 and 14 herein, and their homologs, and (ii) modifying a sequence of the endogenous gene in the plant cell via genome editing or site-directed integration to modify, augment, or increase the expression level of the endogenous gene; and (b) regenerating or developing a plant from the plant cell.

DETAILED DESCRIPTION

In the attached sequence listing:

SEQ ID NOs 1 to 9 are nucleotide sequences or DNA coding sequences or strands that may be used in recombinant DNA constructs to impart an enhanced trait in plants, each representing a coding sequence for a protein.

SEQ ID NOs 10 to 18 are amino acid sequences encoded by the nucleotide or DNA sequences of SEQ ID NOs 1 to 9, respectively in the same order.

SEQ ID NOs 19 to 29 are nucleotide or DNA sequences that may be used in recombinant DNA constructs to impart an enhanced trait or altered phenotype in plants, each representing a promoter with a specific type of expression pattern.

SEQ ID NOs 30 to 39 are amino acid sequences of proteins homologous to proteins having the amino acid sequences of SEQ ID NOs 10 to 18.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotide of the DNA with uracil (U) nucleotide. Thus, providing a specific DNA sequence is understood to define the exact RNA equivalent. A given first polynucleotide sequence, whether DNA or RNA, further defines the sequence of its exact complement (which can be DNA or RNA), i.e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. As used herein, "operably linked" means the association of two or more DNA fragments in a recombinant DNA construct so that the expression or function of one (for example, protein-encoding DNA), is controlled or influenced by the other (for example, a promoter). A first nucleic acid sequence is "operably" connected or "linked" with a second nucleic acid sequence when the first nucleic acid sequence is placed in a functional relationship with the second nucleic acid sequence. For example, a promoter sequence is "operably linked" to DNA if the promoter provides for transcription or expression of the DNA. Generally, operably linked DNA sequences are contiguous.

As used herein, the terms "percent identity" and "percent identical" (including any numerical percentage identity) in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For percent identity, two or more polynucleotide or protein sequences are optimally aligned if the maximum number of ordered nucleotides or amino acids of the two or more sequences are linearly aligned or matched (i.e., identical) with allowance for gap(s) in their alignment. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the terms "percent complementarity" or "percent complementary" (including any numerical percentage complementarity) in reference to two nucleotide sequences is similar to the concept of percent identity, but refers to the percentage of nucleotides of a query sequence that optimally base-pair or hybridize to nucleotides of a subject sequence when the query and subject sequences are linearly arranged and optimally base paired. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. The term "target gene" as used in the context of suppression refers to a "target protein" and/or "target mRNA". In alternative non-limiting embodiments, suppression of a target protein and/or target polynucleotide can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby affect the altered phenotype or enhanced trait indirectly.

Suppression can be applied using numerous approaches. Non-limiting examples include: suppressing an endogenous gene(s) or a subset of genes in a pathway, suppressing one or more mutation(s) that has/have resulted in decreased activity of a protein, suppressing the production of an inhibitory agent, to elevate, reduce or eliminate the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. The term "target gene" as used in the context of overexpression refers to a "target protein" and/or "target mRNA". In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides and/or polypeptides under the control of a promoter, examples of which include but are not limited to endogenous promoters, heterologous promoters, inducible promoters and tissue specific promoters. In one exemplary embodiment, the promoter is a constitutive promoter, for example, the cauliflower mosaic virus 35S transcription initiation region. Thus, depending on the promoter used, overexpression can occur throughout a plant, in specific tissues of the plant, or in the presence or absence of different inducing or inducible agents, such as hormones or environmental signals.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by *Agrobacterium*-mediated transformation, by bombardment using microparticles coated with recombinant DNA, or by other means, such as site-directed integration. A plant cell of this disclosure can be an originally-transformed plant cell or a progeny plant cell that is regenerated into differentiated tissue, for example, into a transgenic plant with stably-integrated, recombinant DNA, or plant part, seed or pollen derived from a transgenic plant or a progeny plant thereof. As used herein, a "transgenic plant" and a "transgenic plant part" mean a plant or plant part, respectively, having in the genome of at least one cell of such plant or plant part a stably-integrated, recombinant DNA construct or sequence introduced using a transformation method.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a heterozygous or hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, increased yield and altered phenotypes as shown in Tables 6-8 and 10-15. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically important characteristics, more specifically increased yield. More specifically the present disclosure relates to a transgenic plant comprising a recombinant polynucleotide of this disclosure, wherein the plant has increased yield as compared to a control plant. Many plants of this disclosure exhibited increased yield or improved yield trait components as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), flowering time and duration, grain fill period. Root architecture and development, photosynthetic efficiency, nutrient uptake, stress tolerance, early vigor, delayed senescence and functional stay green phenotypes can be important factors in determining yield. Optimizing the above-mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear and number of kernels per row, kernel number or weight per ear, weight per kernel, ear number, ear weight, fresh or dry ear biomass (weight)

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having altered phenotype, enhanced trait, or increased yield; performance of the method gives plants altered phenotype, enhanced trait, or increased yield.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds. In one embodiment, increased yield can be increased seed yield, and is selected from one or more of the following: (i) increased seed weight; (ii) increased number of filled seeds; and (iii) increased harvest index.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of altering phenotype, enhancing trait, or increasing yield in a plant by producing a plant comprising a polynucleic acid sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA construct, transgenic plants can be prepared by crossing a first plant having a stably integrated recombinant DNA construct with a second plant lacking the DNA. For example, recombinant DNA can be introduced into a first plant line that is amenable to transformation to produce a transgenic plant which can be crossed with a second plant line to introgress the recombinant DNA into the second plant line.

Selected transgenic plants transformed with a recombinant DNA construct and having the polynucleotide of this disclosure provides the altered phenotype, enhanced trait, or increased yield compared to a control plant. Use of genetic markers associated with the recombinant DNA can facilitate production of transgenic progeny that is homozygous for the desired recombinant DNA. Progeny plants carrying DNA for both parental traits can be back-crossed into a parent line multiple times, for example usually 6 to 8 generations, to produce a progeny plant with substantially the same genotype as the one reoccurring original transgenic parental line but having the recombinant DNA of the other transgenic parental line. The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, a oligonucleotide, or any fragment thereof. In many instances, a polynucleotide encodes a polypeptide (or protein) or a domain or a fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing. In certain embodiments, fragments of any of SEQ ID NO: 1-9 are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or at least about 1250 contiguous nucleotides, or at least about 1500 contiguous nucleotides, or at least about 1750 contiguous nucleotides, or at least about 2000 contiguous nucleotides, or at least about 2250 contiguous nucleotides, or at least about 2500 contiguous nucleotides, or at least about 2750 contiguous nucleotides, or longer, of any of SEQ ID NO: 1-9, and having activity as disclosed herein. Further provided are fragments of any of SEQ ID NOs: 10-18 and 30-39 are provided comprising at least about at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous amino acids, or longer, of any of SEQ ID NO: 10-18 and 30-39, and having activity as disclosed herein.

A "recombinant DNA construct" as used in the present disclosure comprises at least one expression cassette having a promoter operable in plant cells and a polynucleotide of the present disclosure. DNA constructs can be used as a means of delivering recombinant DNA constructs to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 93%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 93%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions (UTRs) and their complements. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. For example, a "seed enhanced" or "seed preferred" promoter drives enhanced or higher expression levels of an associated transgene or transcribable nucleotide sequence (i.e., operably linked to the promoter) in seed tissues relative to other tissues of the plant, whereas a "seed specific" promoter would drive expression of an associated transgene or transcribable nucleotide sequence (i.e., operably linked to the promoter) in seed tissues with little or no expression in other tissues of the plant. Other types of tissue specific or tissue preferred promoters for other tissue types, such as roots, meristem, leaf, etc., may also be described in this way. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Examples of seed preferred or seed specific promoters include promoters from genes expressed in seed tissues, such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2): 157-166, globulin 1 as disclosed by Belanger et al (1991) *Genetics* 129:863-872, glutelin 1 as disclosed by Russell (1997) supra, and peroxiredoxin antioxidant (Per1) as disclosed by Stacy et al. (1996) *Plant Mol Biol.* 31(6):1205-1216. The contents and disclosures of each of the above references are incorporated herein by reference. Examples of meristem preferred or meristem specific promoters are provided, for example, in International Application No. PCT/US2017/057202, the contents and disclosure of which are incorporated herein by reference.

Many examples of constitutive promoters that may be used in plants are known in the art, such as a cauliflower mosaic virus (CaMV) 35S and 19S promoter (see, e.g., U.S. Pat. No. 5,352,605), an enhanced CaMV 35S promoter, such as a CaMV 35S promoter with Omega region (see, e.g., Holtorf, S. et al., *Plant Molecular Biology*, 29: 637-646 (1995) or a dual enhanced CaMV promoter (see, e.g., U.S. Pat. No. 5,322,938), a Figwort Mosaic Virus (FMV) 35S promoter (see, e.g., U.S. Pat. No. 6,372,211), a *Mirabilis Mosaic* Virus (MMV) promoter (see, e.g., U.S. Pat. No. 6,420,547), a Peanut Chlorotic Streak Caulimovirus promoter (see, e.g., U.S. Pat. No. 5,850,019), a nopaline or octopine promoter, a ubiquitin promoter, such as a soybean polyubiquitin promoter (see, e.g., U.S. Pat. No. 7,393,948), an *Arabidopsis* S-Adenosylmethionine synthetase promoter (see, e.g., U.S. Pat. No. 8,809,628), etc., or any functional portion of the foregoing promoters, the contents and disclosures of each of the above references are incorporated herein by reference.

Examples of constitutive promoters that may be used in monocot plants, such as cereal or corn plants, include, for example, various actin gene promoters, such as a rice Actin 1 promoter (see, e.g., U.S. Pat. No. 5,641,876; see also SEQ ID NO: 75 or SEQ ID NO: 76) and a rice Actin 2 promoter (see, e.g., U.S. Pat. No. 6,429,357; see also, e.g., SEQ ID NO: 77 or SEQ ID NO: 78), a CaMV 35S or 19S promoter (see, e.g., U.S. Pat. No. 5,352,605; see also, e.g., SEQ ID NO: 79 for CaMV 35S), a maize ubiquitin promoter (see, e.g., U.S. Pat. No. 5,510,474), a *Coix lacryma-jobi* polyubiquitin promoter (see, e.g., SEQ ID NO: 80), a rice or maize Gos2 promoter (see, e.g., Pater et al., The Plant Journal, 2(6): 837-44 1992; see also, e.g., SEQ ID NO: 81 for the rice Gos2 promoter), a FMV 35S promoter (see, e.g., U.S. Pat. No. 6,372,211), a dual enhanced CMV promoter (see, e.g., U.S. Pat. No. 5,322,938), a MMV promoter (see, e.g., U.S. Pat. No. 6,420,547; see also, e.g., SEQ ID NO: 82), a PCLSV promoter (see, e.g., U.S. Pat. No. 5,850,019; see also, e.g., SEQ ID NO: 83), an Emu promoter (see, e.g., Last et al., Theor. Appl. Genet. 81:581 (1991); and Mcelroy et al., Mol. Gen. Genet. 231:150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that may be used in monocot or cereal plants, and any functional sequence portion or truncation of any of the foregoing promoters. The contents and disclosures of each of the above references are incorporated herein by reference.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an *Arabidopsis* EPSPS gene in the present disclosure, see Klee, H. J. Et al (*MGG* (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e. g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR sequence and termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a non-translated RNA, in the sense or antisense direction, a miRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

As used herein, the term "heterologous" refers to the combination of two or more components, including DNA molecules, when such a combination is not normally found in nature. For example, the two DNA molecules may be derived from different species and/or the two DNA molecules may be derived from different genes, e.g., different genes from the same species or the same genes from different species, or one of the DNA molecules might be synthetic and not found in nature. A first DNA molecule is heterologous with respect to an operably linked second DNA molecule if such a combination is not normally found in nature, i.e., the second DNA molecule does not naturally occur operably linked to the first element.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tins 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in U.S. Patent Application Publication 2002/0192813 A1; and the pea (*Pisum sativum*) ribulose biphosphate carboxylase gene (rbs 3'), and 3' elements from genes within the host plant.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans).

Any site or locus within the genome of a plant may potentially be chosen for site-directed integration of a transgene, construct or transcribable DNA sequence provided herein. Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at or near the site of the DSB or nick. The presence of the homology arm(s) in the donor template may promote the adoption and targeting of the insertion sequence into the plant genome during the repair process through homologous recombination, although an insertion event may also occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

As used herein, the term "homology arm" refers to a polynucleotide sequence that has at least 80%, at least 85%, at least 90%, at least 91%, at least 92%, at least 93%, at least 94%, at least 95%, at least 96%, at least 97%, at least 98%, at least 99% or 100% sequence identity to a target sequence in a plant or plant cell that is being transformed. A homology arm can comprise at least 15, at least 20, at least 25, at least 30, at least 40, at least 50, at least 100, at least 250, at least 500, or at least 1000 nucleotides.

As used herein "operably linked" means the association of two or more DNA fragments in a recombinant DNA construct so that the expression or function of one (for example, protein-encoding DNA), is controlled or influenced by the other (for example, a promoter).

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells that are transformed with a recombinant DNA of this disclosure can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus* thuringensis to provide resistance against lepidopteran, coleopteran, homopteran, hemipteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil, norflurazon, 2,4-D (2,4-dichlorophenoxy) acetic acid, aryloxyphenoxy propionates, p-hydroxyphenyl pyruvate dioxygenase inhibitors (HPPD), and protoporphyrinogen oxidase inhibitors (PPO) herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent No. Application Publication 2003/0083480 A1 also for imparting glyphosate tolerance; dicamba monooxygenase disclosed in U.S. Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260. Molecules and methods for imparting insect/nematode/virus resistance are disclosed in U.S. Pat. Nos. 5,250,515; 5,880,275; 6,506, 599; 5,986,175 and U.S. Patent Application Publication 2003/0150017 A1.

Plant Cell Transformation Methods

Numerous methods for transforming chromosomes and plastids in a plant cell with a recombinant DNA, and/or introducing a recombinant DNA into chromosomes and plastids of a plant cell, are known in the art that may be used in methods of producing a transgenic plant cell and plant. Two effective methods for transformation are *Agrobacterium*-mediated transformation and microprojectile bombardment-mediated transformation. Microprojectile bombardment methods are illustrated, for example, in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described, for example, in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 8,044,260 (cotton); U.S. Pat. No. 6,384,301 (soybean), U.S. Pat. No. 7,026,528 (wheat) and U.S. Pat. No. 6,329,571 (rice), U.S. Patent Application Publication No. 2004/0087030 A1 (cotton), and U.S. Patent Application Publication No. 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

As introduced above, another method for transforming plant cells and chromosomes in a plant cell is via insertion of a DNA sequence using a recombinant DNA donor template at a pre-determined site of the genome by methods of site-directed integration. Site-directed integration may be accomplished by any method known in the art, for example, by use of zinc-finger nucleases, engineered or native meganucleases, TALE-endonucleases, or an RNA-guided endonuclease (for example Cas9 or Cpf1). The recombinant DNA construct may be inserted at the pre-determined site by homologous recombination (HR) or by non-homologous end joining (NHEJ). In addition to insertion of a recombinant DNA construct into a plant chromosome at a pre-determined site, genome editing can be achieved through oligonucleotide-directed mutagenesis (ODM) (Oh and May, 2001; U.S. Pat. No. 8,268,622) or by introduction of a double-strand break (DSB) or nick with a site specific nuclease, followed by NHEJ or repair. The repair of the DSB or nick may be used to introduce insertions or deletions at the site of the DSB or nick, and these mutations may result in the introduction of frame-shifts, amino acid substitutions, and/or an early termination codon of protein translation or alteration of a regulatory sequence of a gene. Genome editing may be achieved with or without a donor template molecule.

In addition to direct transformation of a plant material with a recombinant DNA construct, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield or other yield component trait, can be crossed with a transgenic plant line having another recombinant DNA that confers another trait, for example herbicide resistance or pest resistance, to produce progeny plants having recombinant DNA sequences that confer both traits. The progeny of these crosses may segregate, such that some of the plants will carry the recombinant DNA for both parental traits and some will carry the recombinant DNA for one of the parental traits; and such plants can be identified by one or both of the parental traits and/or markers associated with one or both of the parental traits or the recombinant DNA. For example, marker identification may be performed by analysis or detection of the recombinant DNA, or in the case where a selectable marker is linked to the recombinant DNA, by application of a selection agent, such as a herbicide for use with a herbicide tolerance marker, or by selection for the enhanced trait, or using any molecular technique. Progeny plants carrying DNA for both parental traits can be crossed back to one of the parent lines multiple times, for example 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA construct into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708; 6,118,047 and 8,030,544. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to develop or regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microEinsteins $m^{-2}$ $s^{-1}$ of light, prior to transfer to a greenhouse or growth chamber for maturation. Plants may be regenerated from about 6 weeks to 10 months after a transformant is identified, depending on the initial tissue, and plant species. Plants can be pollinated using conventional plant breeding methods known to those of skill in the art to produce seeds, for example cross-pollination and self-pollination are commonly used with transgenic corn and other plants. The regenerated transformed plant or its progeny seed or plants can be tested for expression of the recombinant DNA and selected for the presence of an altered phenotype or an enhanced agronomic trait.

Transgenic Plants and Seeds

Transgenic plants derived from transgenic plant cells having a transgenic nucleus of this disclosure are grown to generate transgenic plants having an altered phenotype or an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of sequences of protein-encoding genes as recombinant DNA for production of transgenic plants with enhanced traits. The elements of Table 1 are described by reference to: "NUC SEQ ID NO." which identifies a DNA sequence; "PEP SEQ ID NO." which identifies an amino acid sequence; "Gene ID" which refers to an identifier for the gene; and "Gene Name and Description" which is a common name and functional description of the gene.

TABLE 1

Sequences for Protein-Coding Genes

| NUC SEQ ID NO. | PEP SEQ ID NO. | Gene ID | Gene Name and Description |
|---|---|---|---|
| 1 | 10 | TX7G1 | *Agrobacterium tumefaciens* Isopentyl transferase (AGRtu.IPT) |
| 2 | 11 | TX7G2 | Soybean 14-3-3-like protein A gene (Gm.SGF14A) |
| 3 | 12 | TX7G3 | *Nostoc* sp. sucrose-phosphate phosphatase (sppA) |
| 4 | 13 | TX7G4 | Corn isopropylmalate synthase |
| 5 | 14 | TX7G5 | *Arabidopsis thaliana* tonoplast monosaccharide transporter1 gene (At.TMT1) |
| 6 | 15 | TX7G6 | *Chlamydomonas reinhardtii* S-adenosyl-L-homocysteine hydrolase |
| 7 | 16 | TX7G7 | Truncated corn sucrose phosphate synthase gene (Zm.SPS truncated) |
| 8 | 17 | TX7G8 | *Arabidopsis thaliana* vacuolar glucose transporter 1 gene (At.VGT1) |
| 9 | 18 | TX7G9 | *Arabidopsis thaliana* KURZ UND KLEIN gene (At.KUK1) |

Table 2 provides a list of constructs with specific expression pattern, for expression or suppression of protein-coding genes, as recombinant DNA for production of transgenic plants with enhanced traits. The elements of Table 2 are described by reference to: "Construct ID" which identifies a construct with a particular expression pattern by a promoter operably linked to a polynucleotide sequence either expressing or suppressing a protein-coding gene. "Gene ID" which identifies either an expressed or suppressed gene from Table 1 or Table 2. "Specific Expression Pattern" which describes the expected expression pattern or promoter type.

TABLE 2

Constructs for Gene expression

| Construct ID | Gene ID | Specific Expression Pattern |
|---|---|---|
| TX7G1c01 | TX7G1 | Meristem Preferred |
| TX7G1c02 | TX7G1 | Meristem Preferred |
| TX7G1c03 | TX7G1 | Constitutive |
| TX7G1c04 | TX7G1 | Seed Preferred |
| TX7G1c05 | TX7G1 | Seed Preferred |
| TX7G1c06 | TX7G1 | Root Preferred |
| TX7G1c07 | TX7G1 | Ovule & Early Kernel Preferred |
| TX7G1c08 | TX7G1 | Root Preferred |
| TX7G1c09 | TX7G1 | Constitutive |
| TX7G1c10 | TX7G1 | Embryo Scutellum Preferred |
| TX7G1c11 | TX7G1 | Drought Responsive in Leaf & Root |
| TX7G1c12 | TX7G1 | Meristem Preferred |
| TX7G2c1 | TX7G2 | Constitutive |

TABLE 2-continued

Constructs for Gene expression

| Construct ID | Gene ID | Specific Expression Pattern |
| --- | --- | --- |
| TX7G2c2 | TX7G2 | Constitutive |
| TX7G2c3 | TX7G2 | Constitutive |
| TX7G2c4 | TX7G2 | Drought Responsive |
| TX7G3c1 | TX7G3 | Above Ground Preferred; Medium |
| TX7G3c2 | TX7G3 | Leaf Bundle Sheath & Mesophyll Preferred |
| TX7G3c3 | TX7G3 | Constitutive |
| TX7G3c4 | TX7G3 | Leaf Bundle Sheath & Mesophyll Preferred |
| TX7G3c5 | TX7G3 | Above Ground Preferred; High |
| TX7G4c1 | TX7G4 | Constitutive |
| TX7G5c1 | TX7G5 | Constitutive |
| TX7G5c2 | TX7G5 | Constitutive |
| TX7G5c3 | TX7G5 | Leaf Preferred |
| TX7G6c1 | TX7G6 | Constitutive |
| TX7G7c1 | TX7G7 | Above Ground Preferred; High |
| TX7G7c2 | TX7G7 | Leaf Bundle Sheath & Mesophyll Preferred |
| TX7G8c1 | TX7G8 | Constitutive |
| TX7G8c2 | TX7G8 | Constitutive |
| TX7G9c1 | TX7G9 | Root Preferred |

Table 3 provides a list of polynucleotide sequences of promoters with specific expression patterns. To convey the specific expression patterns, choices of promoters are not limited to those listed in Table 3.

TABLE 3

Promoter sequences and expression patterns

| Nucleotide SEQ ID NO. | Promoter Expression Pattern |
| --- | --- |
| 19 | Above Ground Preferred; High |
| 20 | Above Ground Preferred; Medium |
| 21 | Drought Responsive |
| 22 | Drought Responsive in Leaf & Root |
| 23 | Embryo Scutellum Preferred |
| 24 | Leaf Bundle Sheath & Mesophyll Preferred |
| 25 | Leaf Preferred |
| 26 | Meristem Preferred |
| 27 | Ovule & Early Kernel Preferred |
| 28 | Root Preferred |
| 29 | Seed Preferred |

Selecting and Testing Transgenic Plants for Enhanced Traits

Within a population of transgenic plants each developed or regenerated from a plant cell with a recombinant DNA, many plants that survive to fertile transgenic plants that produce seeds and progeny plants will not exhibit an enhanced agronomic trait. Selection from the population may be necessary to identify one or more transgenic plants with an enhanced trait. Further evaluation with vigorous testing may be important for understanding the contributing components to a trait, supporting trait advancement decisions and generating mode of action hypotheses. Transgenic plants having enhanced traits can be selected and tested from populations of plants developed, regenerated or derived from plant cells transformed as described herein by evaluating the plants in a variety of assays to detect an enhanced trait, for example, increased water use efficiency or drought tolerance, enhanced high temperature or cold tolerance, increased yield or yield components, desirable architecture, optimum life cycle, increased nitrogen use efficiency, enhanced seed composition such as enhanced seed protein and enhanced seed oil.

These assays can take many forms including, but not limited to, direct screening for the trait in a greenhouse or field trial or by screening for a surrogate trait. Such analyses can be directed to detecting changes in the chemical composition, biomass, yield components, physiological property, root architecture, morphology, or life cycle of the plant. Changes in chemical compositions such as nutritional composition of grain can be detected by analysis of the seed composition and content of protein, free amino acids, oils, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in yield components can be measured by total number of kernels per unit area and its individual weight. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in root architecture can be evaluated by root length and branch number. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Changes in morphology can also be measured with morphometric analysis based on shape parameters, using dimensional measurement such as ear diameter, ear length, kernel row number, internode length, plant height, or stem volume. Changes in life cycle can be measured by macro or microscopic morphological changes partitioned into developmental stages, such as days to pollen shed, days to silking, leaf extension rate. Other selection and testing properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield can be identified by screening using progenies of the transgenic plants over multiple locations for several years with plants grown under optimal production management practices and maximum weed and pest control or standard agronomic practices (SAP). Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance can be identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method may be changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, *quinoa* and sugar cane plants.

EXAMPLES

Example 1. Corn Transformation

This example illustrates transformation methods to produce a transgenic corn plant cell, seed, and plant having altered phenotypes as shown in Tables 5-7, and enhanced traits, increased water use efficiency, increased nitrogen use efficiency, and increased yield and altered traits and phenology as shown in Tables 9, 10, 12 and 13.

For *Agrobacterium*-mediated transformation of corn embryo cells, ears from corn plants were harvested and surface-sterilized by spraying or soaking the ears in ethanol, followed by air drying. Embryos were isolated from individual kernels of surface-sterilized ears. After excision, maize embryos were inoculated with *Agrobacterium* cells containing plasmid DNA with the gene of interest cassette and a plant selectable marker cassette, and then co-cultured with *Agrobacterium* for several days. Co-cultured embryos were transferred to various selection and regeneration media, and transformed R0 plants were recovered 6 to 8 weeks after initiation of selection, which were transplanted into potting soil. Regenerated R0 plants were selfed, and R1 and subsequent progeny generations were obtained.

The above process can be repeated to produce multiple events of transgenic corn plants from cells that were transformed with recombinant DNA constructs identified in Table 2. Progeny transgenic plants and seeds of the transformed plants were screened for the presence and single copy of the inserted gene, and for various altered or enhanced traits and phenotypes, such as increased water use efficiency, increased yield, and increased nitrogen use efficiency as shown in Tables 5-7 and 9, 10, 12 and 13. From each group of multiple events of transgenic plants with a specific recombinant DNA from Table 2, the event(s) that showed increased yield, increased water use efficiency, increased drought tolerance, increased nitrogen use efficiency, and altered phenotypes and traits were identified.

Example 2. Soybean Transformation

This example illustrates plant transformation in producing a transgenic soybean plant cell, seed, and plant having an altered phenotype or an enhanced trait, such as increased nitrogen use efficiency, increased water use efficiency, increased drought tolerance, and increased yield as shown in Table 13.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA having the constructs identified in Table 2. Progeny transgenic plants and seed of the transformed plants were screened for the presence and single copy of the inserted gene, and tested for various altered or enhanced phenotypes and traits as shown in Tables 11, 12 and 13.

Example 3. Identification of Altered Phenotypes in Automated Greenhouse

This example illustrates screening and identification of transgenic corn plants for altered phenotypes in an automated greenhouse (AGH). The apparatus and the methods for automated phenotypic screening of plants are disclosed, for example, in U.S. Patent Publication No. 2011/0135161, which is incorporated herein by reference in its entirety.

Corn plants were tested in three screens in the AGH under different conditions including non-stress, nitrogen deficit, and water deficit stress conditions. All screens began with non-stress conditions during days 0-5 germination phase, after which the plants were grown for 22 days under the screen-specific conditions shown in Table 4.

TABLE 4

Description of the three AGH screens for corn plants

| Screen | Description | Germination Phase (5 days) | Screen Specific Phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

Water deficit is defined as a specific Volumetric Water Content (VWC) that is lower than the VWC of a non-stressed plant. For example, a non-stressed plant might be maintained at 55% VWC, and the VWC for a water-deficit assay might be defined around 30% VWC. Data were collected using visible light and hyperspectral imaging as well as direct measurement of pot weight and amount of water and nutrient applied to individual plants on a daily basis.

Nitrogen deficit is defined (in part) as a specific mM concentration of nitrogen that is lower than the nitrogen concentration of a non-stressed plant. For example, a non-stressed plant might be maintained at 8 mM nitrogen, while the nitrogen concentration applied in a nitrogen-deficit assay might be maintained at a concentration of 2 mM.

Up to ten parameters were measured for each screen. The visible light color imaging based measurements are: biomass, canopy area, and plant height. Biomass (Bmass) is defined as the estimated shoot fresh weight (g) of the plant obtained from images acquired from multiple angles of view. Canopy Area (Cnop) is defined as leaf area as seen in a top-down image ($mm^2$). Plant Height (PlntH) refers to the distance from the top of the pot to the highest point of the plant derived from a side image (mm). Anthocyanin score and area, chlorophyll score and concentration, and water content score are hyperspectral imaging-based parameters. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Chlorophyll Concentration (ClrpC) are both measurements of chlorophyll in the leaf canopy obtained from a top-down hyperspectral image, where Chlorophyll Score measures in relative units, and Chlorophyll Concentration is measured in parts per million (ppm) units. Water Content Score (WtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment to maintain a stable soil water content.

These physiological screen runs were set up so that tested transgenic lines were compared to a control line. The collected data were analyzed against the control using % delta and certain p-value cutoff. Tables 5, 6 and 7 are summaries of transgenic corn plants comprising the disclosed recombinant DNA constructs with altered phenotypes under non stress, nitrogen deficit, and water deficit conditions, respectively. "ConstructID" refers to the construct identifier as defined in Table 2.

The test results are represented by three numbers: the first number before letter "p" denotes number of events with an increase in the tested parameter at $p \leq 0.1$; the second number before letter "n" denotes number of events with a decrease in the tested parameter at $p \leq 0.1$; the third number before letter "t" denotes total number of transgenic events tested for a given parameter in a specific screen. The increase or decrease is measured in comparison to non-transgenic control plants. A designation of "-" indicates that it has not been tested. For example, 2p1n5t indicates that 5 transgenic plant events were screened, of which 2 events showed an increase, and 1 showed a decrease of the measured parameter.

TABLE 5

Summary of transgenic plants with altered phenotypes in AGH non-stress screens.

| ConstructID | AntS | Bmass | Cnop | ClrpS | PlntH | WtrAp | WtrCt | WUE |
| --- | --- | --- | --- | --- | --- | --- | --- | --- |
| TX7G3c3 | 0p0n8t | 0p0n8t | 1p1n8t | 0p2n8t | 0p1n8t | 3p2n8t | 0p0n8t | 0p0n8t |

TABLE 6

Summary of transgenic plants with altered phenotypes in AGH nitrogen-deficit screens.

| ConstructID | AntA | AntS | Bmass | Cnop | ClrpC | ClrpS | PlntH | WtrAp | WtrCt | WUE |
| --- | --- | --- | --- | --- | --- | --- | --- | --- | --- | --- |
| TX7G3c3 | — | 0p0n8t | 3p0n8t | 3p0n8t | — | 2p1n8t | 2p0n8t | 3p0n8t | 2p2n8t | 3p0n8t |
| TX7G1c09 | 0p0n5t | 1p0n5t | 0p1n5t | 0p2n5t | 0p0n5t | — | 1p0n5t | 0p1n5t | — | 0p1n5t |
| TX7G3c4 | 0p0n5t | 0p0n5t | 1p0n5t | 1p0n5t | 0p0n5t | — | 0p0n5t | 0p2n5t | — | 1p0n5t |

TABLE 7

Summary of transgenic plants with altered phenotypes in AGH water-deficit screens.

| ConstructID | AntA | AntS | Bmass | Cnop | ClrpC | ClrpS | PlntH | WtrAp | WtrCt | WUE |
| --- | --- | --- | --- | --- | --- | --- | --- | --- | --- | --- |
| TX7G3c3 | — | 0p1n8t | 0p3n8t | 0p3n8t | — | 1p0n8t | 0p2n8t | 2p4n8t | 2p3n8t | 0p2n8t |
| TX7G3c4 | 1p0n5t | 0p0n5t | 0p1n5t | 0p2n5t | 0p1n5t | — | 0p0n5t | 0p1n5t | — | 0p2n5t |

Example 4. Evaluation of Transgenic Plants for Trait Characteristics

Trait assays were conducted to evaluate trait characteristics and phenotypic changes in transgenic plants as compared to non-transgenic controls. Corn and soybean plants were grown in field and greenhouse conditions. Up to 18 parameters were measured for corn in phenology, morphometrics, biomass, and yield component studies at certain plant developmental stages. For root assays, soybean plants were grown in the greenhouse in transparent nutrient medium to allow the root system to be imaged and analyzed.

Corn developmental stages are defined by the following development criteria:
Developed leaf: leaf with a visible leaf collar;
V-Stages: Number of developed leaves on a corn plant corresponds to the plant's vegetative growth stage—i.e., a V6 stage corn plant has 6 developed (fully unfolded) leaves;

R1 (Silking): Plants defined as R1 must have one or more silks extending outside the husk leaves. Determining the reproductive stage of the crop plant at R1 or later is based solely on the development of the primary ear;

R3 (Milk): Typically occurs 18-22 days after silking depending on temperature and relative maturity. Kernels are usually yellow in color and the fluid inside each kernel is milky white;

R6 (Physiological maturity): Typically occurs 55-65 days after silking (depending on temperature and relative maturity group of the germplasm being observed). Kernels have reached their maximum dry matter accumulation at this point, and kernel moisture is approximately 35%.

Soybean developmental stages are defined by criteria as following:

Fully developed trifoliate leaf node: A leaf is considered completely developed when the leaf at the node immediately above it has unrolled sufficiently so the two edges of each leaflet are no longer touching. At the terminal node on the main stem, the leaf is considered completely developed when the leaflets are flat and similar in appearance to older leaves on the plant;

VC: Cotyledons and Unifoliolates are fully expanded;

R1: Beginning of flowering—i.e., one open flower at any node on the main stem.

Table 8 describes the trait assays. TraitRefID is the reference ID of each trait assay. Trait Assay Name is the descriptive name of the assay. The Description provides what the assay measures, and how the measurement is conducted. Direction For Positive Call indicates whether an increase or decrease in the measurement quantity corresponds to a "positive" call in the assay results.

TABLE 8

Description of Trait Assays

| TraitRefID | Trait Assay Name | Description | Direction For Positive Call |
|---|---|---|---|
| HINDXR6 | Harvest Index at R6 | Ratio of grain weight to total plant weight at harvest. Weights are determined on a dry weight basis. | Increase |
| DBMSR6 | Dry Biomass by Seed at R6 | Ratio of grain weight to total plant weight at R6 stage. Weights are determined on a dry weight basis. | Increase |
| AGDWR6 | Total Dry Biomass at R6 | Total aboveground oven-dried biomass at R6. Plants are cut at ground level, oven-dried at 70 deg. C. to a constant weight, and weighed. | Increase |
| DFL50 | Days from Planting to 50% Flowering | Days from Planting to 50% Flowering | Neutral |
| PDPPR8 | Number of Pods per Plant at R8 | Total pods per soybean plant. Quotient of count of pods from plants in a defined linear distance (20") on a plot row divided by number of plants. | Increase |
| PDNODER8 | Pods per Node at R8 | Total pods per flowering node on a soybean plant. Quotient from count of pods on plants in a defined linear distance (20") on a plot row divided by count of nodes on those plants. | Increase |
| ARDR2 | Average Root Diameter at R2 | Estimated average diameter of all root classes of root at R2 stage, using WinRHIZO (TM) image analysis system software. | Increase |
| RBNR2 | Root branch number at R2 | Number of root branches per plant determined by automated analysis of digitized root images from field root digs. | Increase |
| DOV12 | Days from Planting to V12 | number of days from the date of planting to the date when 50% of the plants in a plot reaches V12 stage. | Decrease |
| EAR6 | Ear Area at R6 | plot average of size of area of a ear from a 2-dimentional view. The measurement is done through imaging of ear, including kernels and void. Typically 10 representative ears are measured per plot. Measurement is taken at R6 stage. | Increase |
| EDR6 | Ear Diameter at R6 | plot average of the ear diameter. It measures maximal "wide" axis over the ear on the largest section of the ear. Measurement is taken at R6 stage. | Increase |
| EDWR1 | Ear Dry Weight at R6 | plot average of the ear dry weight of a plant. Measurement is taken at R6 stage. | Increase |
| ELR6 | Ear Length at R6 | plot average of the length of ear. It measures from tip of ear in a straight line to the base at the ear node. Measurement is taken at R6 stage. | Increase |
| ETVR6 | Ear Tip Void Percentage at R6 | plot average of area percentage of void at the top 30% area of a ear, from a 2-dimentional view. The measurement is done through imaging of ear, including kernels and void. Typically 10 representative ears are measured per plot. Measurement is taken at R6 stage. | Decrease |

TABLE 8-continued

Description of Trait Assays

| TraitRefID | Trait Assay Name | Description | Direction For Positive Call |
|---|---|---|---|
| EVR6 | Ear Void Percentage at R6 | plot average of area percentage of void on a ear, from a 2-dimentional view. The measurement is done through imaging of ear, including kernels and void. Typically 10 representative ears are measured per plot. Measurement is taken at R6 stage. | Decrease |
| KPER6 | Kernels per Ear at R6 | plot average of the number of kernels per ear. It is calculated as (total kernel weight/(Single Kernel Weight * total ear count), where total kernel weight and total ear count are measured from ear samples from an area between 0.19 to 10 square meters, and Single Kernel Weight (SKWTR6) is described below. Measurement is taken at R6 stage. | Increase |
| KRLR6 | Kernels per Row Longitudinally at R6 | (also known as rank number) the plot average of the number of kernels per row longitudinally. It is calculated as the ratio of (total kernel count per ear)/(kernel row number). Measurement is taken at R6 stage. | Increase |
| KRNR6 | Kernel Row Number at R6 | plot average of the number of rows of kernels on an ear, by counting around the circumference of the ear. Measurement is taken at R6 stage. | Increase |
| LFTNR3 | Leaf Tip Number at R3 | plot average of the number of leaves per plant, by counting the number of leaf tips. Measurement is taken at R3 stage. | Increase |
| P50DR1 | Days to 50% Pollen Shedding | number of days from the date of planting to the date when 50% of the plants in a plot reaches Pollen Shed stage. | Decrease |
| PHTR3 | Plant Height at R3 | plot average of plant height. It measures from soil line to base of highest collared leaf. Measurement is taken at R3 stage. | Decrease |
| PLTHGR | Plant Height Growth Rate from V6 to V12 | plot average of growth rate of a plant from V6 to V12 stage. It is calculated as (Plant Height measured at V12-Plant Height measured at V6)/Days between measurements. | Increase |
| RBPN | Root Branch Point Number at VC or V2 | number of root branch tip points of a plant. The measurement is done through imaging of the root system of a plant grown in a transparent Gelzan(TM) gum gel nutrient medium to VC stage for soybean, or to V2 stage for corn. The root system image is skeletonized for the root length measurement. Up to 40 images are taken at various angles around the root vertical axis and measurement is averaged over the images. Gelzan is a trademark of CP Kelco U.S., Inc. | Increase |
| RTL | Root Total Length at VC or V2 | cumulative length of roots of a plant, as if the roots were all lined up in a row. The measurement is done through imaging of the root system of a plant grown in a transparent Gelzan(TM) gum gel nutrient medium to VC stage for soybean, or to V2 stage for corn. The root system image is skeletonized for the root length measurement. Up to 40 images are taken at various angles around the root vertical axis and measurement is averaged over the images. Gelzan is a trademark of CP Kelco U.S., Inc. | Increase |
| S50DR1 | Days to 50% Visible Silk | number of days from the date of planting to the date when 50% of the plants in a plot reaches visible Silking (R1) stage. | Decrease |
| SKWTR6 | Single Kernel Weight at R6 | plot average of weight per kernel. It is calculated as the ratio of (sample kernel weight adjusted to 15.5% moisture)/(sample kernel number). The sample kernel number ranges from 350 to 850. Measurement is taken at R6 stage. | Increase |
| STDIR3 | Stalk Diameter at R3 | plot average of the stalk diameter of a plant. It measures maximal "long" axis in the middle of the internode above first visible node. Measurement is taken at R3 stage. | Increase |

TABLE 8-continued

Description of Trait Assays

| TraitRefID | Trait Assay Name | Description | Direction For Positive Call |
|---|---|---|---|
| EDWPPR6 | Ear Dry Weight Per Plant at R6 | plot average of the ear dry weight of a plant. Measurement is taken at R6 stage. | Increase |
| SPPR8 | Seeds per Plant at R8 | The number of seeds per plant at developmental stage R8 (maturity stage) | Increase |
| SW1000 | Weight of 1000 seeds | The weight of one thousand seeds | Increase |
| PDDWR6 | Pod Dry Weight at R6 | The weight of hand harvested pods from a plot at developmental stage R6 | Increase |

These trait assays were set up so that the tested transgenic lines were compared to a control line. The collected data were analyzed against the control, and positives were assigned if there was a p-value of 0.2 or less. Tables 9-12 are summaries of transgenic plants comprising the disclosed recombinant DNA constructs for corn phenology and morphometrics assays, corn yield/trait component assays, soybean phenology and morphometrics, and yield/trait component assays, and corn and soybean root assays, respectively.

The test results are represented by three numbers: the first number before letter "p" denotes number of tests of events with a "positive" change as defined in Table 9; the second number before letter "n" denotes number of tests of events with a "negative" change which is in the opposite direction of "positive" as defined in Table 8; the third number before letter "t" denotes total number of tests of transgenic events for a specific assay for a given gene. The "positive" or "negative" change is measured in comparison to non-transgenic control plants. A designation "-" indicates that it has not been tested. For example, 2p1n5t indicates that 5 transgenic plant events were tested, of which 2 events showed a "positive" change and 1 showed a "negative" change of the measured parameter. The assay is indicated with its TraitRefID as in Table 8.

TABLE 9

Summary of assay results for corn phenology and morphometric trait assays.

| Construct ID | P50DR1 | S50DR1 | KRNR6 | KRLR6 |
|---|---|---|---|---|
| TX7G1c07 | — | — | 0p4n8t | 0p2n8t |
| TX7G1c10 | — | — | 2p4n8t | 0p2n8t |
| TX7G5c1 | 1p0n4t | 1p1n4t | — | — |
| TX7G3c3 | 6p2n10t | 2p0n10t | 0p8n10t | 0p0n10t |

TABLE 10

Summary of results for corn trait component assays.

| Construct ID | EAR6 | EDR6 | EDWPPR6 | ERDWAR6 | ELR6 |
|---|---|---|---|---|---|
| TX7G1c07 | 0p2n8t | 2p2n8t | — | — | 0p2n8t |
| TX7G1c10 | 0p6n8t | 0p4n8t | — | — | 0p6n8t |
| TX7G8c2 | 0p1n4t | 0p1n4t | 0p0n4t | 0p0n4t | 0p0n4t |
| TX7G5c1 | 1p5n16t | 1p3n16t | 2p1n12t | 0p3n12t | 1p2n16t |
| TX7G3c3 | 6p0n19t | 0p13n19t | 0p2n4t | 2p0n4t | 11p0n19t |
| TX7G3c4 | 0p1n4t | 0p1n4t | 0p1n4t | 0p0n4t | 0p1n4t |
| TX7G5c3 | 0p2n7t | 0p2n7t | 1p1n7t | 0p1n7t | 0p1n7t |

| Construct ID | ETVR6 | EVR6 | HINDXR6 | KPER6 | SKWTR6 | AGDWR6 |
|---|---|---|---|---|---|---|
| TX7G1c07 | 0p0n8t | 0p0n8t | — | 0p2n8t | 0p0n8t | — |
| TX7G1c10 | 4p0n8t | 4p0n8t | — | 0p4n8t | 0p4n8t | — |
| TX7G8c2 | 2p0n4t | 2p0n4t | 0p0n4t | 0p0n4t | 1p0n4t | 0p1n4t |
| TX7G5c1 | 7p0n16t | 5p0n16t | 9p5n28t | 0p1n16t | 0p3n16t | 0p2n12t |
| TX7G3c3 | 4p4n23t | 12p0n24t | 0p2n4t | 2p2n19t | 3p0n19t | 2p0n4t |
| TX7G3c4 | 0p2n8t | 0p0n8t | 0p0n4t | 1p1n4t | 0p2n4t | 0p0n4t |
| TX7G5c3 | 3p1n7t | 4p0n7t | 2p0n7t | 0p1n7t | 2p1n7t | 0p1n7t |

TABLE 11

Summary of results for soybean phenology, morphometrics and trait component assays.

| Construct ID | DBMSR6 | PDPPR8 | PHTR8 | PDDWR6 | PDNODER8 | SW1000 | SPPR8 | AGDWR6 |
|---|---|---|---|---|---|---|---|---|
| TX7G3c5 | 0p0n8t | — | — | 4p3n12t | — | 0p6n12t | 0p5n12t | 4p3n12t |
| TX7G5c2 | — | — | — | — | — | 2p0n4t | 0p1n4t | 0p1n4t |
| TX7G8c1 | — | — | — | — | — | 0p1n4t | 0p0n4t | 0p0n4t |
| TX7G9c1 | — | — | — | — | — | 0p1n6t | 0p1n6t | — |
| TX7G7c1 | 0p0n8t | — | — | 0p0n8t | — | 0p6n8t | 0p2n8t | 4p0n8t |

TABLE 11-continued

Summary of results for soybean phenology, morphometrics and trait component assays.

| Construct ID | DBMSR6 | PDPPR8 | PHTR8 | PDDWR6 | PDNODER8 | SW1000 | SPPR8 | AGDWR6 |
|---|---|---|---|---|---|---|---|---|
| TX7G1c04 | — | 0p3n4t | 0p4n4t | — | 0p4n4t | 2p0n4t | 0p4n4t | — |
| TX7G1c01 | — | 0p4n4t | 0p4n4t | — | 1p1n4t | 4p0n4t | 0p4n4t | — |
| TX7G1c02 | — | 0p2n4t | 2p1n4t | — | 2p1n4t | 1p1n4t | 0p1n4t | — |
| TX7G6c1 | — | — | — | — | — | 0p4n8t | 2p2n8t | 0p2n8t |
| TX7G1c03 | — | 0p4n4t | 0p2n4t | — | 0p4n4t | 4p0n4t | 0p4n4t | — |

TABLE 12

Summary of results for corn and soybean root assays.

| Crop | Construct ID | RTL | RBPN |
|---|---|---|---|
| Corn | TX7G1c09 | 0p1n4t | 0p3n4t |
| Soybean | TX7G9c1 | 2p0n4t | 2p0n4t |

Example 5. Phenotypic Evaluation of Transgenic Plants in Field Trials for Increased Nitrogen Use Efficiency, Increased Water Use Efficiency, and Increased Yield Corn field trials were conducted to identify genes that can improve nitrogen use efficiency (NUE) under nitrogen limiting conditions leading to increased yield performance as compared to non transgenic controls. For the Nitrogen field trial results shown in Table 13, each field was planted under nitrogen limiting condition (60 lbs/acre), and corn ear weight or yield was compared to non-transgenic control plants.

Corn field trials can be conducted to identify genes that can improve water use efficiency (WUE) under water limiting conditions leading to increased yield performance as compared to non transgenic controls. The corn ear weight or yield can be compared to non-transgenic control plants.

Corn and soybean field trials were conducted to identify genes that can improve broad-acre yield (BAY) under standard agronomic practice. Results of the broad-acre yield trials conducted under standard agronomic practice are shown in Table 13, and the corn or soybean yield was compared to non-transgenic control plants.

Table 13 provides a list of genes that produce transgenic plants having increased nitrogen use efficiency (NUE), and/ or increased broad-acre yield (BAY) as compared to a control plant. Polynucleotide sequences in constructs with at least one event showing significant yield or ear weight increase across multiple locations at p≤0.2 are included. The genes were expressed with constitutive promoters unless noted otherwise under the "Specific Expression Pattern" column. A promoter of a specific expression pattern was chosen over a constitutive promoter, based on the understanding of the gene function, or based on the observed lack of significant yield increase when the gene was expressed with constitutive promoter. The elements of Table 13 are described as follows: "Crop" refers to the crop in trial, which is either corn or soybean; "Condition" refers to the type of field trial, which is BAY for broad acre yield trial under standard agronomic practice (SAP), and NUE for nitrogen use efficiency trial; "Construct ID" refers to the construct identifier as defined in Table 2; "Gene ID" refers to the gene identifier as defined in Table 1; "Yield results" refers to the recombinant DNA in a construct with at least one event showing significant yield increase at p≤0.2 across locations. The first number refers to the number of tests of events with significant yield or ear weight increase, whereas the second number refers to the total number of tests of events for each recombinant DNA in the construct. Typically 4 to 8 distinct events per construct are tested.

TABLE 13

Yield and nitrogen use efficiency with protein-coding transgenes.

| Crop | Condition | Construct ID | Gene ID | Yield Results |
|---|---|---|---|---|
| Soybean | BAY | TX7G3c1 | TX7G3 | 3/18 |
| Corn | BAY | TX7G3c2 | TX7G3 | 2/18 |
| Corn | BAY | TX7G3c3 | TX7G3 | 13/49 |
| Corn | NUE | TX7G3c3 | TX7G3 | 2/8 |
| Soybean | BAY | TX7G2c2 | TX7G2 | 0/8 |
| Corn | BAY | TX7G3c4 | TX7G3 | 0/8 |
| Soybeans | BAY | TX7G7c1 | TX7G7 | 0/6 |
| Soybean | BAY | TX7G2c3 | TX7G2 | 4/18 |
| Corn | BAY | TX7G2c4 | TX7G2 | 0/6 |

Example 6. Homolog Identification

This example illustrates the identification of homologs of proteins encoded by the DNA sequences identified in Table 1, which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Tables 14 and 15.

Table 14 provides a list of homolog genes, the elements of which are described as follows: "PEP SEQ ID NO." identifies an amino acid sequence. "Homolog ID" refers to an alphanumeric identifier, the numeric part of which is the NCBI Genbank GI number; and "Gene Name and Description" is a common name and functional description of the gene. Table 15 describes the correspondence between the protein-coding genes in Table 1 and their homologs, and the level of protein sequence alignment between the gene and its homolog.

Example 7. Use of Site-Directed Integration to Introduce Transgenes or Modulate Expression of Endogenous Genes in Plants As introduced above, a DNA sequence comprising a transgene(s), expression cassette(s), etc., such as one or more coding sequences of genes identified in Tables 1, 2 and 15, or homologs thereof, may be inserted or integrated into a specific site or locus within the genome of a plant or plant cell via site-directed integration. Recombinant DNA constructs and molecules of this disclosure may thus include a donor template having an insertion sequence comprising at least one transgene, expression cassette, or other DNA sequence for insertion into the genome of the plant or plant cell. Such donor template for site-directed integration may further include one or two homology arms flanking the insertion sequence to promote insertion of the insertion sequence at the desired site or locus. Any site or locus within the genome of a plant may be chosen for site-directed integration of the insertion sequence. Several methods for site-directed integration are known in the art involving

TABLE 14

Homologous gene information

| PEP SEQ ID NO. | Homolog ID | Gene Name and Description |
|---|---|---|
| 30 | gi_1495273 | gi|1495273|emb|CAA90628.1| sugar transporter [*Arabidopsis thaliana*] |
| 31 | gi_255645592 | gi|255645592|gb|ACU23290.1| [Glycine max] |
| 32 | gi_15219062 | gi|15219062|ref|NP_176240.1| F-box family protein, containing similarity to MYB transcription factor isolog T01O24.1 [*Arabidopsis thaliana*] |
| 33 | gi_4586310 | gi|4586310|dbj|BAA76344.1| isopentenyl transferase [*Agrobacterium tumefaciens*] |
| 34 | gi_10955004 | gi|10955004|ref|NP_053424.1| hypothetical protein pTi-SAKURA_p186, isopentenyl transferase [*Agrobacterium tumefaciens*] |
| 35 | gi_226529888 | gi|226529888|ref|NP_001146891.1| 2-isopropylmalate synthase B [Zea mays] |
| 36 | gi_5042196 | gi|5042196|emb|CAB44641.1| isopentenyl transferase [*Agrobacterium tumefaciens*] |
| 37 | gi_255638346 | gi|255638346|gb|ACU19485.1| [Glycine max] |
| 38 | gi_4836905 | gi|4836905|gb|AAD30608.1|AC007369_18 Sugar transporter [*Arabidopsis thaliana*] |
| 39 | gi_3023194 | gi|3023194|sp|Q96450|1433A_SOYBN 14-3-3-like protein A; AltName: SGF14A [Glycine max] |

TABLE 15

Correspondence of Genes and Homologs

| Gene ID | Homolog ID | Percent Gene Coverage | Percent Homolog Coverage | Percent Identity |
|---|---|---|---|---|
| TX7G1 | gi_10955004 | 100 | 100 | 99 |
| TX7G1 | gi_5042196 | 100 | 100 | 99 |
| TX7G1 | gi_4586310 | 100 | 100 | 97 |
| TX7G2 | gi_255645592 | 100 | 100 | 98 |
| TX7G2 | gi_255638346 | 100 | 100 | 98 |
| TX7G2 | gi_3023194 | 100 | 100 | 98 |
| TX7G4 | gi_226529888 | 100 | 100 | 98 |
| TX7G5 | gi_4836905 | 100 | 100 | 99 |
| TX7G5 | gi_1495273 | 100 | 100 | 97 |
| TX7G9 | gi_15219062 | 100 | 100 | 99 | different proteins (or complexes of proteins and/or guide RNA) that cut the genomic DNA to produce a double strand break (DSB) or nick at a desired genomic site or locus. Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome. The recombinant DNA molecules or constructs of this disclosure may further comprise an expression cassette(s) encoding a site-specific nuclease, a guide RNA, and/or any associated protein(s) to carry out the desired site-directed integration event.

The endogenous genomic loci of a plant or plant cell corresponding to the genes identified in Tables 1 and 14, or a homolog thereof, may be selected for site-specific insertion of a recombinant DNA molecule or sequence capable of modulating expression of the corresponding endogenous genes. As described above, the recombinant DNA molecule or sequence serves as a donor template for integration of an insertion sequence into the plant genome. The donor template may also have one or two homology arms flanking the insertion sequence to promote the targeted insertion event. Although a transgene, expression cassette, or other DNA sequence may be inserted into a desired locus or site of the plant genome via site-directed integration, a donor template may instead be used to replace, insert, or modify a 5' untranslated region (UTR), upstream sequence, promoter, enhancer, intron, 3' UTR and/or terminator region of an endogenous gene, or any portion thereof, to modulate the expression level of the endogenous gene. Another method for modifying expression of an endogenous gene is by genome editing of an endogenous gene locus. For example, a targeted genome editing event may be made to disrupt or abolish a regulatory binding site for a transcriptional repressor of an endogenous gene to increase or modify expression of the endogenous gene.

For genome editing or site-specific integration of an insertion sequence of a donor template, a double-strand break (DSB) or nick is made in the selected genomic locus. The DSB or nick may be made with a site-specific nuclease, for example a zinc-finger nuclease, an engineered or native meganuclease, a TALE-endonuclease, or an RNA-guided endonuclease (for example Cas9 or Cpf1). In the presence of a donor template, the DSB or nick may be repaired by homologous recombination between the homology arms of the donor template and the plant genome, resulting in site-directed integration of the insertion sequence to make a targeted genomic modification or insertion at the site of the DSB or nick. For genes shown herein to cause or produce a desired phenotype or trait in a plant, an expression construct or transgene comprising the coding sequence of the gene operably linked to a plant expressible promoter may be inserted at a desired or selected site within the genome of the plant via site-directed integration as discussed above. Alternatively, the sequence of a corresponding endogenous gene, such as within a regulatory region of the endogenous gene, may be modified via genome editing or site-directed integration to augment or alter the expression level of the endogenous gene, such as by adding a promoter or intron sequence, or by modifying or replacing a 5' UTR sequence, promoter, enhancer, transcription factor or repressor binding site, intron, 3' UTR sequence, and/or terminator region, or any portion thereof, of the endogenous gene.

Following transformation of a plant cell with a recombinant molecule(s) or construct(s), the resulting events are screened for site-directed insertion of the donor template insertion sequence or genome modification. Plants containing these confirmed edits, events or insertions may then be tested for modulation of an endogenous gene, expression of an integrated transgene and/or modification of yield traits or other phenotypes.

The invention claimed is:

1. A recombinant DNA construct comprising:
   a) a polynucleotide sequence with at least 95% identity to SEQ ID NO:5; or
   b) a polynucleotide sequence that encodes a polypeptide comprising an amino acid sequence with at least 95% identity to SEQ ID NO:14;
   wherein the polynucleotide sequence of part a) or part b) is operably linked to a leaf preferred promoter comprising SEQ ID NO:25.

2. A vector or plasmid comprising the recombinant DNA construct of claim 1.

3. A plant comprising the recombinant DNA construct of claim 1.

4. The plant of claim 3, wherein the plant is a field crop.

5. The plant of claim 4, wherein the field crop plant is selected from the group consisting of corn, soybean, cotton, canola, rice, barley, oat, wheat, turf grass, alfalfa, sugar beet, sunflower, quinoa and sugarcane.

6. The plant of claim 3, wherein the plant has an altered phenotype or an enhanced trait as compared to a control plant.

7. The plant of claim 6, wherein the enhanced trait is selected from the group consisting of: decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant.

8. The plant of claim 6, wherein the altered phenotype is selected from the group consisting of plant height, biomass, canopy area, anthocyanin content, chlorophyll content, water applied, water content, and water use efficiency.

9. A plant part or propagule comprising the recombinant DNA construct of claim 1, wherein the plant part or propagule is selected from the group consisting of cells, pollen, ovule, flower, embryo, leaf, root, stem, shoot, meristem, grain and seed.

10. A method for altering a phenotype, enhancing a trait, increasing yield, increasing nitrogen use efficiency, or increasing water use efficiency in a plant comprising producing a transgenic plant comprising a recombinant DNA construct of claim 1.

11. The method of claim 10, wherein the recombinant DNA construct further comprises a heterologous promoter functional in a plant cell and operably linked to the polynucleotide sequence of the recombinant DNA construct.

12. The method of claim 10, wherein the transgenic plant is produced by transforming a plant cell or tissue with the recombinant DNA construct, and regenerating or developing the transgenic plant from the plant cell or tissue comprising the recombinant DNA construct.

13. The method of claim 10, further comprising:
producing a progeny plant comprising the recombinant DNA construct by crossing the transgenic plant with:
   a) itself;
   b) a second plant from the same plant line;
   c) a wild type plant; or
   d) a second plant from a different plant line,
to produce a seed, growing the seed to produce a progeny plant; and
selecting a progeny plant with increased yield, increased nitrogen use efficiency, or increased water use efficiency as compared to a control plant.

14. The method of claim 10, wherein the transgenic plant is produced by site-directed integration of the recombinant DNA construct into the genome of a plant cell or tissue using a donor template comprising the recombinant DNA construct, and regenerating or developing the transgenic plant from the plant cell or tissue comprising the recombinant DNA construct.

15. A plant produced by the method of claim 10.

16. A recombinant DNA molecule for use as a donor template in site-directed integration, wherein the recombinant DNA molecule comprises an insertion sequence comprising:
   a) a polynucleotide sequence with at least 95% identity to SEQ ID NO:5; or
   b) a polynucleotide sequence that encodes a polypeptide comprising an amino acid sequence with at least 95% identity to SEQ ID NO:14;
wherein the polynucleotide sequence of part a) or part b) is operably linked to a leaf preferred promoter comprising SEQ ID NO:25.

17. The recombinant DNA molecule of claim 16, wherein the insertion sequence further comprises a heterologous promoter functional in a plant cell and operably linked to the polynucleotide sequence.

18. The recombinant DNA molecule of claim 16, further comprising at least one homology arm flanking the insertion sequence.

19. The recombinant DNA molecule of claim 16, wherein the recombinant DNA molecule further comprises at least one cassette encoding site-specific nuclease, wherein the site specific nuclease is selected from the group comprising zinc-finger nuclease, an engineered or native meganuclease, a TALE endonuclease, or an RNA-guided endonuclease.

20. The recombinant DNA molecule of claim 16, wherein the recombinant DNA molecule further comprises at least one cassette encoding one or more guide RNAs.

21. The recombinant DNA construct of claim 16, wherein the insertion sequence comprises a promoter, an enhancer, an intron, or a terminator region.

22. The recombinant DNA construct of claim 1, wherein the recombinant DNA construct comprises a polynucleotide sequence with at least 95% identity to SEQ ID NO:5.

23. The recombinant DNA construct of claim 1, wherein the recombinant DNA construct comprises a polynucleotide sequence with at least 97% identity to SEQ ID NO:5.

24. The recombinant DNA construct of claim 1, wherein the recombinant DNA construct comprises a polynucleotide sequence that encodes a polypeptide comprising an amino acid sequence with at least 97% identity to SEQ ID NO:14.

25. The recombinant DNA construct of claim 1, wherein the recombinant DNA construct comprises a polynucleotide sequence comprising SEQ ID NO:5.

26. The recombinant DNA construct of claim 1, wherein the recombinant DNA construct comprises a polynucleotide sequence that encodes a polypeptide comprising an amino acid sequence comprising SEQ ID NO:14.

* * * * *

SEQUENCE LISTING

```
Sequence total quantity: 39
SEQ ID NO: 1            moltype = DNA  length = 723
FEATURE                 Location/Qualifiers
source                  1..723
                        mol_type = other DNA
                        organism = Agrobacterium tumefaciens
SEQUENCE: 1
atggatctgc gtctaatttt cggtccaact tgcacaggaa agacgtcgac cgcggtagct   60
cttgcccagc agactgggct tccagtcctt tcgctcgatc gggtccaatg ttgtcctcag  120
ctgtcaaccg gaagcggacg accaacagtg gaagaactga aaggaacgag ccgtctatac  180
cttgatgatc ggcctctggt gaagggtatc atcgcagcca agcaagctca tgaaaggctg  240
atggggggg tgtataatta tgaggcccac ggcgggctta ttcttgaggg aggatctatc  300
tcgttgctca agtgcatggc gcaaagcagt tattggagtg cggattttcg ttggcatatt  360
attcgccacg agttagcaga cgaagagacc ttcatgaacg tggccaaggc cagagttaag  420
cagatgttac gccctgctgc aggcctttct attatccaag agttggttga tctttggaaa  480
gagcctcggc tgaggcccat actgaaagag atcgatggat atcgatatgc catgttgttt  540
gctagccaga accagatcac atccgatatg ctattgcagc ttgacgcaga tatggaggat  600
aagttgattc atgggatcgc tcaggagtat ctcatccatg cacgccgaca agaacagaaa  660
ttccctcgag ttaacgcagc cgcttacgac ggattcgaag gtcatccatt cggaatgtat  720
tag                                                                723

SEQ ID NO: 2            moltype = DNA  length = 774
FEATURE                 Location/Qualifiers
source                  1..774
                        mol_type = other DNA
                        organism = Glycine max
SEQUENCE: 2
atggcggatt cttctcggga ggagaacgtt tacatggcga aattggcgga gcaggccgag   60
cgttacgagg agatggttga gttcatggag aaggttgcaa agactgtgga ggttgaggag  120
ttgacggtgg aggagaggaa tctcctctct gtggcttaca agaacgtgat tggtgcgagg  180
agggcttcgt ggaggatcat atcctccatt gagcagaagg aggagagcag gggcaatgag  240
gaccacgtgg ccattataaa ggagtacagg ggcaaaattg aggctgaact cagcaagatc  300
tgtgatggga ttttgaacct ccttgagtcc aacctcattc cttccgctgc atctcccgag  360
agcaaagtct tttaccttaa aatgaagggt gattaccaca ggtaccttgc tgagttcaag  420
accggggcag agaggaaaga ggctgcagag agtactttgc ttgcttacaa atccgctcag  480
gatattgctc ttgctgactt ggcccccact cacccatta ggtgggact tgctctcaac  540
ttttctgtgt tctattatga aatccttaac tcgccagatc gtgcttgtaa tcttgccaag  600
caggcatttg atgaggcaat ttccgagctt gacacattgg gtgaagagtc atacaaagat  660
agtacattga tcatgcaact tctccgtgac aatctgactt tgtggacatc agacatcacg  720
gacgatgctg gagatgagat caaggaaaca tctaagcaac aaccaggcga atag         774

SEQ ID NO: 3            moltype = DNA  length = 750
FEATURE                 Location/Qualifiers
source                  1..750
                        mol_type = other DNA
```

```
                         organism = Nostoc sp. PCC 7120
SEQUENCE: 3
atgaagccat ttcttttgt caccgatttg gatcatactc tggtaggtaa tgatgcagcc    60
ctggcagaac tcagccagat actcactcac catcgtcaag aatatggcac aaagatagtt   120
tatgccactg ggcgatcgcc tattctttac aaagaactgc aagtagaaaa aaacctgata   180
gaacctgatg ggttagtttt gtctgtgggt acggaaatct atcttgatgg tagtggtaat   240
cctgattctg actggtcaga aattcttaac gatggctgga atcgagaact agtattgtcc   300
gtaactaaaa aatttcctga attaatgctg caaccagact cggaacaacg tccttttaaa   360
gtcagttttt ttctgcatca agaagcctca tttaaggtca taccacaact tgagacagag   420
ttagcgaaat gtaaactaaa tataaagtta atttatagta gcggtataga ccttgacatt   480
gtaccattaa acagcgataa aggtcaggca atgcagtttc ttcgtcaaaa gtggaaattt   540
gcagcagaaa gaacagttgt ctgtggtgat tcaggtaatg atattgcttt gttcgctgtg   600
ggcaacgaaa ggggaatcat cgtcgggaat gcccgaccgg agttgcttca gtggcacagt   660
gagtatcccg cagaccatcg ctacctggca aaaaactttt gtgcaggtgg aattattgaa   720
ggtttacaat tctttggttt cctcgaatag                                    750

SEQ ID NO: 4        moltype = DNA  length = 1881
FEATURE             Location/Qualifiers
source              1..1881
                    mol_type = other DNA
                    organism = Zea mays
SEQUENCE: 4
atggcgtcct cgctgctctc ctcccccgct aaacccacca tcaccaccac caccaaaacg    60
accccggccc caagaccccgc ccgctccgcc catgtccatg tcctctccgc cgcccgctgc   120
ctccgcctcc gcctccgcgc gtcgtcgcag catcctccgc ctccgccccac cccgcggtcg   180
cggcggccgg attacgtccc gaaccgcatc gacgacccca actacgtgcg catcttcgac   240
accacgctgc gcgacgggga gcagtcgccg ggcgccacca tgacgagcgg ccagaagctc   300
gtcgtcgcgc gccagctggc ccgctcggc gtcgacatca tcgaggccgg gttcccggcc   360
tcctcccccg acgacctcga cgccgtgcgc tccatcgcca tcgaggtcgg caacccggcg   420
ccaggaccg ccggggagga ggacgccgtc cacgtgccgg tcatctgcgg cctctcgccg   480
tgcaaccgga aggacatcga cgccgcgtgg gaggccgtcg gccacgcgcg ccgccccgcg   540
atccacacct tcatcgccac cagcgacatt cacatgcagc ataagctcag gaagacgccc   600
gaccaggtgg tcgccattgc cagggagatg gtggcctacg cccgcagcct cggatgcact   660
gacgtcgagt tcagcccccga ggacgccggc aggtcaaata gagagttctt gtatcatatt   720
ctaggggaag tcataaaagc tggagctacg actctcaata tcccggacac tgtcggatac   780
aatcttcctt atgaatttgg aaagttgatt gctgatataa aggcaaacac tcctggaatt   840
gaaaaggcta tcatttccac tcattgtcag aatgaccttg tcttgcgac tgccaacaca   900
ctagcgggcg ctcgtgcagg agcacggcag ttagaggtta ctattaatgg tattggtgaa   960
agggctggaa atgcttcttt ggaggaggtt gtcatggcaa ttaaatgccg cagagaactg  1020
ttagatggtc tctatactgg aatcgattcc cgacatatca ctttgacgca caaaatggtg  1080
caagagcata gtggacttca cgtgcagcca cataaagcta ttgttggtgc caatgcgttc  1140
gctcatgaaa gtggaattca tcaggatggg atgcttaaat ataaggaac atacgaaatt  1200
atatcgcctg atgatattgg tctaacacgt gcaaatgaat ttggtattgt tcttgggaaa  1260
ctcagcggaa ggcatgctgt gagatctaag ctagtagagc ttggatatga aatcggtgac  1320
aaggaattg aggacttctt taaacgctac aaagaggttg cagagaagaa aaagcgcgta  1380
actgatgaag acttagaagc gttattgtca gatgagatat tccagcctaa ggttatttgg  1440
tcccttgctg atgtacaggc aacatgtggt acacttgctt tatctacggc aacagtgaaa  1500
ttggtagcac cagatggaga ggagaaaata gcatgttcag tcggaacagg tccagtcgat  1560
gcagcttaca aggctgttga caaaataatc cagattccaa cggttctccg agaatacagt  1620
atgacatcag tcagaaagg cattgacgca atcgcgacaa ctcgggttgt tgtcactgga  1680
gatgtgagca acaacgccaa acatgccctg actggccagt ccttcaaccg ctccttcagt  1740
gggagcgggg catccatgga cattgtggtg tccagtgtca gagcttacct gagcgccctg  1800
aacaagatct gcagtttcgc tggcgccgtg aaagcccagca gcgatgtagc tgagaccgca  1860
agcgtccccga gcacagaatg a                                           1881

SEQ ID NO: 5        moltype = DNA  length = 2205
FEATURE             Location/Qualifiers
source              1..2205
                    mol_type = other DNA
                    organism = Arabidopsis thaliana
SEQUENCE: 5
atgaagggag cgactctcgt tgctctcgcc gccacaatcg gcaatttctt acaaggatgg    60
gacaatgcca ccattgctgg agctatggtt tatatcaaca aagacttgaa tctaccaacc   120
tctgttcaag gtcttgtcgt tgctatgtca ttgatcggtca cacgacttgc                180
tcaggaccga tatctgattg gctcggcaga cgcccatgc tcattttatc atcagttatg   240
tatttcgtct gcggtttgat aatgttgtgg tctcccaatg tctatgttct gtgctttgct   300
aggcttctta atgggtttgg tgccgggctc gcggttacac ttgtccctgt ttacatttct   360
gaaaccgctc ctccggagat cagaggcag ttaaatctaa tccctcagtt cttggctct   420
ggtggaatgt ttttgtcata ctgtatgtt ttcactatgt ccctgagtga ctccccctagc   480
tggagagcca tgctcggtgt cctctcgatc ccttctcttc tttatttgtt tctccacggtg   540
ttttatttgc ccgagtctcc tcgttggctg gttagtaaag aagaatgga cgaggctaag   600
cgagttcttc aacagttatg tggcagaa gatgttaccg atgagatggc tttactagtt   660
gaaggactag atataggagg agaaaaaaca atggaagatc tcttagtaac tttggaggat   720
catgaaggtg atgatacact tgaaaccgtt gatgaggatg gacaatggg gctttatgga   780
acccacgaga atcaatcgta ccttgctaga cctgtcccag aacaaaatag ctcacttggg   840
ctacgctctc gccacggaag cttagcaaac caaagcatga tccttaaaga tccgctcgtc   900
aatctttttg gcagtctcca cgagaagatg ccagaagcag gcgaaacac tcggagtggg   960
attttcccctc atttcggaag catgttcagt actactgccg atgcgcctca cggtaaaccg  1020
gctcattggg aaaaggacat agagagccat acaacaaag acaatgatga ctatgcgact  1080
```

```
gatgatggtg cgggtgatga tgatgactcg gacaacgatt tgcgtagccc cttaatgtcg 1140
cgccagacca caagcatgga caaggatatg atcccacatc ctacaagtgg aagcacttta 1200
agcatgagac gacacagtac gcttatgcaa ggcaacggcg aaagtagcat gggaattggt 1260
ggtggttggc atatgggata tagatacgaa aacgatgaat acaagaggta ttatcttaaa 1320
gaagatggag ctgaatctcg ccgtggctcg atcatctcta ttcccggagg tccggatggt 1380
ggaggcagct acattcacgc ttctgccctt gtaagcagat ctgttcttgg tcctaaatca 1440
gttcatggat ccgccatggt tccccgagag aaaattgctg cctctggacc actctggtct 1500
gctcttcttg aacctggtgt taagcgtgcc ttggttgttg gtgtcggcat tcaaatactg 1560
cagcagtttt caggtatcaa tggagttctc tactacactc ctcagattct cgaacgggct 1620
ggcgtagata ttcttctttc gagcctcgga ctaagttcca tctctgcgtc attcctcatc 1680
agcggtttaa caacattact catgctccca gccattgtcg ttgccatgag actcatggat 1740
gtatccggaa gaaggtcatt acttctctgg acaatcccag ttctcattgt ctcacttgtc 1800
gtccttgtca tcagcgagct catccacatc agcaaagtcg tgaacgcagc actctccaca 1860
ggttgtgtcg tgctctactt ctgcttcttc gtgatggatt acggtcccat tccaaacatc 1920
ctctgttctg aaatcttccc aacaagagtc cgtggtctct gcatcgccat atgtgctatg 1980
gtcttttgga ttggagacat tatttgtcacg tactcacttc ccgttctcct cagctcgatc 2040
ggactagttg gtgttttcag catttacgct gcggtttgcg ttatctcatg gatcttcgtt 2100
tacatgaaag tcccggagac taaaggcatg cctttggaag ttatcacaga ctactttgcc 2160
tttggagctc aagctcaagc ttctgctcct tctaaggata tataa      2205

SEQ ID NO: 6           moltype = DNA   length = 216
FEATURE                Location/Qualifiers
source                 1..216
                       mol_type = other DNA
                       organism = Chlamydomonas reinhardtii
SEQUENCE: 6
atgggtgaag cggttctcat ctgctttagt ggagtgtctt gtggcgggtg tagaagggca  60
tggagatcca ctcatgctgt tgaatgttcc ggagcattac aaagacttgc ggtcgcagcc 120
ggtgctgtta tgcaagatgc gcgcgagcgt agagggatcg tgtgcactta catcaagcag 180
tatgggaacg gagcagagcc ctgtcctgca caatga                           216

SEQ ID NO: 7           moltype = DNA   length = 2760
FEATURE                Location/Qualifiers
source                 1..2760
                       mol_type = other DNA
                       organism = synthetic construct
SEQUENCE: 7
atggcattcc agaggaactt ctctgacctt accgtctggt ccgacgacaa taaggagaag  60
aagctttaca ttgtgctcat cagtgtgcat ggtcttgttc gtggcgaaaa catggaacta 120
ggtcgtgatt ctgacaccgg tggccaggtg aaatatgttg tcgaacttgc aagagcaatg 180
tcaatgatgc ctggagtgta cagggtggac ctcttcactc gtcaagtgtc atctcctgac 240
gtggactgga gctatggtga gccgaccgag atgttatgct ccggttccaa cgatggagag 300
gggatgggta agagtgccgg agcctacatt gtgcgcatac cgtgtgagcc acggataaa  360
tatctcaaga aggaagcact gtggccttac ctccaagagt ttgtcgatgg agctcttgcg 420
catattctta acatgtccaa ggctctggga gagcaggttg gaaatgggag ccagtactgc 480
ccttacgtga tacatggaca ctatgccgac gctggagatg ttgctgctct cctttccggt 540
gcgctcaatg tacccatggt gctgactggt cactcacttg ggaggaacaa gctggagcaa 600
atcctgaagc aagggcgcat gtccaaggag gagatcgatt caacatacaa gatcatgagg 660
cgtatcgagg gtgaggagct ggccctggat gcgtcagagc ttgtcatcac cagcacaagg 720
caggagattg atgaacagtg gggattgtac gacggatttg atgtcaagct tgagaaagtg 780
ttgagggcac gggcgaggcg tggggttagc tgccatggtc gtttcatgcc taggatggtg 840
gtgattcctc caggaatgga tttcagcaat gttgtggttc atgaagacat tgatggggat 900
ggtgacagca aagatgatat cgttggttttg gagggtgctt cacccaagtc aatgcccca  960
attggccg aggtgatgcg gttcctaacc aatcctcaca gccgatgat cctggcgctg 1020
tcgaggcgag acccgaagaa gaacatcact accctcgtca aagccttgg agagtgccc 1080
ccactcaggg aacttgcaaa ccttactcta atcatgggaa acagagatga catcgacgat 1140
atgtctgctg gcaatgccag tgtcctcacc acagttctga agctgataga caagtatgat 1200
ctgtatggaa gcgtagcgtt tcctaagcat cacaatcagg ctgatgtccc ggagatctac 1260
gccgtcgcgg ccaaaatgaa gggtgtcttc atcaaccctg ctctcgttga gccgttcggt 1320
ctcaccctga tcgaggctgc agcacacgga cttccaatag tcgctaccaa gaatggtgat 1380
ccggtcgaca ttacaactgc actgagcaac ggactgctcg ttgacccgca cgaccagaac 1440
gccatcgctc aagcactgct gaagctcgta gcagataaga acctgtggca ggaatgccgg 1500
agaaacgggc tgcgaaacat ccacctttac tcatggccgg agcactgccg cacttacctc 1560
accaggctg ctgggtgccg gttaaggaac ccagaggtgc tgaaggacac accagcagat 1620
gccgagctg atgaggagga gttcctggag gattccatgg acgctcagga cctgtcactc 1680
cgtctgtcca tcgacggtga aagagctcg ctgaacacca acgaccatt gtcgtcggac 1740
ccgcaggatc aggtgcagaa gatcatgaac aagatcaatc agtcgtcagc acttccgccg 1800
tccatgtcct cagtcgcaga cggtgccaag aacgcaaccg agaccacggg cagcacccttg 1860
aacaagtacc cactccctcg cggccggcgc ctgttcgtca tcgccgtgca ctgctaccaa 1920
gacgacggcc gtgctagcaa gaagatgctg caggtgatcc aggaagtttt cagagcagtc 1980
cgatcggact cccagatgtc caagatctca gggttcgcgc tgtccactgc gatgccgttg 2040
tccgaaacac tccagcttct gcagctcggc aagatcccag cgaccgactt cgacaccctc 2100
atctgtggca gtgcagcga ggtctactat cctggcacag tgaactgcgt cgacgctgaa 2160
ggaaagtgc gccagacca ggactatctg atgcacatga gccaccgctg gccccatgac 2220
ggcgagaagc agaccatagc gaagctcatg gccactcagg acggttcagg cgacactgtc 2280
gagctgacc cggcgtctag taatgcacac tgcttcacgt tccttatcaa agatcccaaa 2340
aaggtgaaaa cggtcgatga tgatgaggag aggctgagga tgcgtggtct ccggtgccac 2400
atcatgtact gcaggaactc gacaaggctt caggttgtcc ctctgctagc atcaaggtca 2460
caggcactca ggtatctttt tgtgcgctgg ggcctatatg tggggaacat gtatctgatc 2520
```

```
actgggaac atggcgacac cgatcatgag gagatgctat ctgggttaca caagactgtg  2580
attgtccggg gtgtcaccga gaaaggttcg gaagggctgc tgaggagccc aggaagctac  2640
aagaaggacg acgtcgtgcc gtctgagacc cccttggctg cgtacacgac tggtgagctg  2700
aaggccgatg agatcatgag ggctctgaaa caagtctcaa agacttccag cggcatgtga  2760
```

SEQ ID NO: 8           moltype = DNA   length = 1512
FEATURE                Location/Qualifiers
source                 1..1512
                       mol_type = other DNA
                       organism = Arabidopsis thaliana
SEQUENCE: 8
```
atggggtttg atcccgagaa ccaatcgatc tcttccgttg acaggttgtt ggtgattct   60
tcttcaggtg ggattactgc tgaaaaggaa cctttgttaa aggaaaacca cagcccagag  120
aactactctg ttcttgcagc cattcctccg tttctcttc cagctcttgg agcattgctt  180
tttggttatg aaattggtgc aacatcttgt gctatcatgt ctcttaagtc gcctactcta  240
agtggaattt catggtacga cttgtcttca gtggatgttg gtataattac cagtggctca  300
ctgtatggtc ccttaattgg ctccattgtt gcatttagtg ttgccgacat tataggaagg  360
agaaaggagc tgattttggc tgcattcttg tatcttgttg gagccattgt gactgtagta  420
gcacctgtct tttccatact gataattgga cgagttacgt atggcatggg gattggactg  480
accatgcacg cggctccaat gtacattgca gagactgctc caagtcaaat acgtggacgg  540
atgatatcac taaaggaatt ctccactgtc cttgggatgt tgggggtta tggaatcggt  600
agcctttgga ttacggttat ttctggttgg cgttacatgt acgcaacaat tctcccttt   660
ccagttatta tgggaactgg aatgtgttgg ctaccagcat ctccgaggtg gcttttactg  720
cgcgctctcc agggacaagg aaatgggag atcttcaac aggctgcgat agatctctt    780
tgtcgcctta gagggtctgt catagctgac tcagcagctg aacaagtaaa cgaaatattg  840
gctgaacttt cccttgtggg tgaagacaaa gaagctacat ttggtgaatt atttcgaggc  900
aaatgcttga aagctctcac tatagcagga gggttagtct tgttccaaca gataactggg  960
caaccaagtg tactatatta tgcaccatca atactacaga ctgccggctt ttctgctgca 1020
gctgatgcaa ctcggatctc aattctgctc ggcctattga agttggttat gacaggagtt 1080
tctgtgatag ttatcgacag agttggaagg agaccttttac ttctttgtgg tgttagcgga 1140
atggtgatct cattgttcct cctgggatcc tactacatgt tttataaaaa tgtaccagct 1200
gttgctgtag ctgcattgct actgtatgta ggctgttacc agctgtcctt tggcccatt   1260
ggttggctga tgatttcaga gatatttccc ttaaaattaa gaggtagagg aatcagtcta 1320
gcagtgcttg tgaattttgg cgcaaacgca cttgtgacat tcgctttctc accgctaaag 1380
gagctgttag gagctggaat actgttctgt gcatttggag tgatatgtgt cgtgtctctc 1440
ttcttcatat actacattgt gccagagaca aagggtctca ctcttgaaga aattgaagcc 1500
aaatgtctct aa                                                     1512
```

SEQ ID NO: 9           moltype = DNA   length = 852
FEATURE                Location/Qualifiers
source                 1..852
                       mol_type = other DNA
                       organism = Arabidopsis thaliana
SEQUENCE: 9
```
atgaacggag gagaaaagtt agaatctatc ccgattgatc tcattattga gatacattca   60
agattaccag cggagtcagt cgcaaggttt cgctgcgtgt cgaagctatg ggggtctatg  120
tttcgccgtc catatttcac cgagctgttc ttgaccagtc gccgtgctcg tccacgtctc  180
ttattcgtcc tccaacacaa ccgtaaatgg agcttcagcg tcttctcttc gcctcaaaat  240
cagaatatat atgtgaagcc gtcttttgta gtagctgatt tcacatgaa gttctctgta   300
agcacgttcc cagattttca tagttgctct ggtttgatcc atttctctat gatgaaaggc  360
gcatataacag tgccggtggt atgtaactct cgcacgtgac aatatgcgtt cctacctaca  420
ctgacaagga caaggtacga aaattcgtat agctttgtag ggtatgatcc gattgagaag  480
caaatcaagg tactgttcat gtctgatcca gatagtggtg atgaccatag aattctgacg  540
ttaggaacaa ctgaaaaaat gttggggagg aagatcgaat gtagcttaac ccataatata  600
ttgtctaatg aaggggtatg catcaatgga gttttgtatt acaaagcttc ccgaattgtt  660
gaatcgtcat ctgacgatga cacgtctgat gatgatgatg atgatcatga acggtctgat  720
gtgattgttt gctttgattt taggtgtgag aaattcgagt ttattgtcat atgctttat   780
ggccagttga taaattccgt ccagttatca ctaaaacaaa aatctcacca gaaacttgac  840
ttaatcatat ag                                                      852
```

SEQ ID NO: 10          moltype = AA    length = 240
FEATURE                Location/Qualifiers
source                 1..240
                       mol_type = protein
                       organism = Agrobacterium tumefaciens
SEQUENCE: 10
```
MDLRLIFGPT CTGKTSTAVA LAQQTGLPVL SLDRVQCCPQ LSTGSGRPTV EELKGTSRLY   60
LDDRPLVKGI IAAKQAHERL MGGVYNYEAH GGLILEGGSI SLLKCMAQSS YWSADFRWHI  120
IRHELADEET FMNVAKARVK QMLRPAAGLS IIQELVDLWK EPRLRPILKE IDGYRYAMLF  180
ASQNQITSDM LLQLDADMED KLIHGIAQEY LIHARRQEQK FPRVNAAAYD GFEGHPFGMY  240
```

SEQ ID NO: 11          moltype = AA    length = 257
FEATURE                Location/Qualifiers
source                 1..257
                       mol_type = protein
                       organism = Glycine max
SEQUENCE: 11
```
MADSSREENV YMAKLAEQAE RYEEMVEFME KVAKTVEVEE LTVEERNLLS VAYKNVIGAR   60
RASWRIISSI EQKEESRGNE DHVAIIKEYR GKIEAELSKI CDGILNLLES NLIPSAASPE  120
```

```
SKVFYLKMKG DYHRYLAEFK TGAERKEAAE STLLAYKSAQ DIALADLAPT HPIRLGLALN   180
FSVFYYEILN SPDRACNLAK QAFDEAISEL DTLGEESYKD STLIMQLLRD NLTLWTSDIT   240
DDAGDEIKET SKQQPGE                                                 257

SEQ ID NO: 12           moltype = AA  length = 249
FEATURE                 Location/Qualifiers
source                  1..249
                        mol_type = protein
                        organism = Nostoc sp. PCC 7120
SEQUENCE: 12
MKPFLFVTDL DHTLVGNDAA LAELSQILTH HRQEYGTKIV YATGRSPILY KELQVEKNLI    60
EPDGLVLSVG TEIYLDGSGN PDSDWSEILN DGWNRELVLS VTKKFPELML QPDSEQRPFK   120
VSFFLHQEAS FKVIPQLETE LAKCKLNIKL IYSSGIDLDI VPLNSDKGQA MQFLRQKWKF   180
AAERTVVCGD SGNDIALFAV GNERGIIVGN ARPELLQWHS EYPADHRYLA KNFCAGGIIE   240
GLQFFGFLE                                                          249

SEQ ID NO: 13           moltype = AA  length = 626
FEATURE                 Location/Qualifiers
source                  1..626
                        mol_type = protein
                        organism = Zea mays
SEQUENCE: 13
MASSLLSSPA KPTITTTTKT TPAPRPARSA HVHVLSAARC LRLRLRASSQ HPPPPPTPRS    60
RRPDYVPNRI DDPNYVRIFD TTLRDGEQSP GATMTSAQKL VVARQLARLG VDIIEAGFPA   120
SSPDDLDAVR SIAIEVGNPA PGPAGEEDAV HVPVICGLSR CNRKDIDAAW EAVRHARRPR   180
IHTFIATSDI HMQHKLRKTP DQVVAIAREM VAYARSLGCT DVEFSPEDAG RSNREFLYHI   240
LGEVIKAGAT TLNIPDTVGY NLPYEFGKLI ADIKANTPGI EKAIISTHCQ NDLGLATANT   300
LAGARAGARQ LEVTINGIGE RAGNASLEEV VMAIKCRREL LDGLYTGIDS RHITLTSKMV   360
QEHSGLHVQP HKAIVGANAF AHESGIHQDG MLKYKGTYEI ISPDDIGLTR ANEFGIVLGK   420
LSGRHAVRSK LVELGYEIGD KEFEDFFKRY KEVAEKKKRV TDEDLEALLS DEIFQPKVIW   480
SLADVQATCG TLALSTATVK LVAPDGEEKI ACSVGTGPVD AAYKAVDKII QIPTVLREYS   540
MTSVTEGIDA IATTRVVVTG DVSNNAKHAL TGQSFNRSFS GSGASMDIVV SSVRAYLSAL   600
NKICSFAGAV KASSDVAETA SVPSTE                                       626

SEQ ID NO: 14           moltype = AA  length = 734
FEATURE                 Location/Qualifiers
source                  1..734
                        mol_type = protein
                        organism = Arabidopsis thaliana
SEQUENCE: 14
MKGATLVALA ATIGNFLQGW DNATIAGAMV YINKDLNLPT SVQGLVVAMS LIGATVITTC    60
SGPISDWLGR RPMLILSSVM YFVCGLIMLW SPNVYVLCFA RLLNGFGAGL AVTLVPVYIS   120
ETAPPEIRGQ LNTLPQFLGS GGMFLSYCMV FTMSLSDSPS WRAMLGVLSI PSLLYLFLTV   180
FYLPESPRWL VSKGRMDEAK RVLQQLCGRE DVTDEMALLV EGLDIGGEKT MEDLLVTLED   240
HEGDDTLETV DEDGQMRLYG THENQSYLAR PVPEQNSSLG LRSRHGSLAN QSMILKDPLV   300
NLFGSLHEKM PEAGGNTRSG IFPHFGSMFS TTADAPHGKP AHWEKDIESH YNKDNDDYAT   360
DDGAGDDDDS DNDLRSPLMS RQTTSMDKDM IPHPTSGSTL SMRRHSTLMQ GNGESSMGIG   420
GGWHMGYRYE NDEYKRYYLK EDGAESRRGS IISIPGGPDG GGSYIHASAL VSRSVLGPKS   480
VHGSAMVPPE KIAASGPLWS ALLEPGVKRA LVVGVGIQIL QQFSGINGVL YYTPQILERA   540
GVDILLSSLG LSSISASFLI SGLTTLLMLP AIVVAMRLMD VSGRRSLLLW TIPVLIVSLV   600
VLVISELIHI SKVVNAALST GCVVLYFCFF VMGYGPIPNI LCSEIFPTRV RGLCIAICAM   660
VFWIGDIIVT YSLPVLLSSI GLVGVFSIYA AVCVISWIFV YMKVPETKGM PLEVITDYFA   720
FGAQAQASAP SKDI                                                    734

SEQ ID NO: 15           moltype = AA  length = 71
FEATURE                 Location/Qualifiers
source                  1..71
                        mol_type = protein
                        organism = Chlamydomonas reinhardtii
SEQUENCE: 15
MGEAVLICFS GVSCGGCRRA WRSTHAVECS GALQRLAVAA GAVMQDARER RGIVCTYIKQ    60
YGNGAEPCPA Q                                                        71

SEQ ID NO: 16           moltype = AA  length = 919
FEATURE                 Location/Qualifiers
source                  1..919
                        mol_type = protein
                        organism = synthetic construct
SEQUENCE: 16
MAFQRNFSDL TVWSDDNKEK KLYIVLISVH GLVRGENMEL GRDSDTGGQV KYVVELARAM    60
SMMPGVYRVD LFTRQVSSPD VDWSYGEPTE MLCSGSNDGE GMGESAGAYI VRIPCGPRDK   120
YLKKEALWPY LQEFVDGALA HILNMSKALG EQVGNGRPVL PYVIHGHYAD AGDVAALLSG   180
ALNVPMVLTG HSLGRNKLEQ ILKQGRMSKE EIDSTYKIMR RIEGEELALD ASELVITSTR   240
QEIDEQWGLY DGFDVKLEKV LRARARRGVS CHGRFMPRMV VIPPGMDFSN VVVHEDIDGD   300
GDSKDDIVGL EGASPKSMPP IWAEVMRFLT NPHKPMILAL SRPDPKKNIT TLVKAFGECP   360
PLRELANLTL IMGNRDDIDD MSAGNASVLT TVLKLIDKYD LYGSVAFPKH HNQADVPEIY   420
AVAAKMKGVF INPALVEPFG LTLIEAAAHG LPIVATKNGG PVDITTALSN GLLVDPHDQN   480
AIAQALLKLV ADKNLWQECR RNGLRNIHLY SWPEHCRTYL TRVAGCRLRN PRWLKDTPAD   540
AGADEEEFLE DSMDAQDLSL RLSIDGEKSS LNTNDPLSSD PQDQVQKIMN KINQSSALPP   600
```

```
SMSSVADGAK NATETTGSTL NKYPLPRGRR LFVIAVDCYQ DDGRASKKML QVIQEVFRAV    660
RSDSQMSKIS GFALSTAMPL SETLQLLQLG KIPATDFDTL ICGSGSEVYY PGTVNCVDAE    720
GKLRPDQDYL MHISHRWSHD GAKQTIAKLM ATQDGSGDTV ELDPASSNAH CFTFLIKDPK    780
KVVKTVDEMRE RLRMRGLRCH IMYCRNSTRL QVVPLLASRS QALRYLFVRW GLYVGNMYLI   840
TGEHGDTDHE EMLSGLHKTV IVRGVTEKGS EGLLRSPGSY KKDDVVPSET PLAAYTTGEL    900
KADEIMRALK QVSKTSSGM                                                 919

SEQ ID NO: 17             moltype = AA  length = 503
FEATURE                   Location/Qualifiers
source                    1..503
                          mol_type = protein
                          organism = Arabidopsis thaliana
SEQUENCE: 17
MGFDPENQSI SSVGQVVGDS SSGGITAEKE PLLKENHSPE NYSVLAAIPP FLFPALGALL     60
FGYEIGATSC AIMSLKSPTL SGISWYDLSS VDVGIITSGS LYGALIGSIV AFSVADIIGR    120
RKELILAAFL YLVGAIVTVV APVFSILIIG RVTYGMGIGL TMHAAPMYIA ETAPSQIRGR    180
MISLKEFSTV LGMVGGYGIG SLWITVISGW RYMYATILPF PVIMGTGMCW LPASPRWLLL    240
RALQGQGNGE NLQQAAIRSL CRLRGSVIAD SAAEQVNEIL AELSLVGEDK EATFGELFRG    300
KCLKALTIAG GLVLFQQITG QPSVLYYAPS ILQTAGFSAA ADATRISILL GLLKLVMTGV    360
SVIVIDRVGR RPLLLCGVSG MVISLFLLGS YYMFYKNVPA VAVAALLLYV GCYQLSFGPI    420
GWLMISEIFP LKLRGRGISL AVLVNFGANA LVTFAFSPLK ELLGAGILFC AFGVICVVSL    480
FFIYYIVPET KGLTLEEIEA KCL                                            503

SEQ ID NO: 18             moltype = AA  length = 283
FEATURE                   Location/Qualifiers
source                    1..283
                          mol_type = protein
                          organism = Arabidopsis thaliana
SEQUENCE: 18
MNGGEKLESI PIDLIIEIHS RLPAESVARF RCVSKLWGSM FRRPYFTELF LTRSRARPRL     60
LFVLQHNRKW SFSVFSSPQN QNIYVKPSFV VADFHMKFSV STFPDFHSCS GLIHFSMMKG    120
AYTVPVVCNS RTGQYAVLPK LTRTRYENSY SFVGYDPIEK QIKVLFMSDP DSGDDHRILT    180
LGTTEKMLGR KIECSLTHNI LSNEGVCING VLYYKASRIV ESSSDDDTSD DDDDDHERSD    240
VIVCFDFRCE KFEFIVICFY GQLINSVQLS LKQKSHQKLD LII                      283

SEQ ID NO: 19             moltype = DNA  length = 1318
FEATURE                   Location/Qualifiers
source                    1..1318
                          mol_type = other DNA
                          organism = synthetic construct
SEQUENCE: 19
atcaacaaat tactcctcaa tcacactcct atagaaaacg gtttaagcta tcattacatg     60
tctagttggt tttactcagc cctagaagtg ttgtttattg catccatttc cacgaagcac    120
aattttctt ttttacaatc accagacctc acaggctcac acatatgctt tagagcacat    180
tctaaacttt gaactataaa agctgttaac actaatacac tatgcgttct ttttttgctcc   240
aaacacttt gatccattat taggagacac tccacttaga aagattttct aatcctttgg    300
tcaactagga agttcaaggt ttttctaaac agaaatttcat ttcacaagta atttaattta   360
taaggaaatg aatagagaaa tcaaatcatt gaagaactac aaaatataga ttcaaggtca    420
ggtctaagaa atattcctg aagctcaaaa aagagttttc ctctcacatt atagaattgg    480
cctttactc aacatttttcc cacctattcc acatttggtc agaacatttt taattacttg    540
tggatcaatt tccggttgaa atgggtttgg tgaatatccg gttcagttat atggtggccg    600
ttggaattgg cttattagtt gtggccgttg ttgaagccgt tggtattggt aagggagaag    660
cagacttgtg gctatgagtc tatgaccatg actcgtgatt atggagctgt cttatgaccc    720
tgaccatcac cttgatctgg tggattccaa tgttttcttc ttcttctaat aaaatattat    780
ggtcaataca ggtgctaatt aagatgataa taatttctta tgtttctgtg gtaaagtttg    840
attcaattcc gtagttttag ataatcttat ttccatacat aaattttata gttttatcta    900
ctttgttctt atgtttttatc tctagcaaag agttattatt attatcagaa gaagaaaaaa    960
aaaagaagca tatatacaaa aggtttaata aaatgtatta tacaaggcaa ttatccaaat   1020
tttttttgtt ttggtttaca ttgatgctct caggatttca taaggataga gagatctatt   1080
cgtatacgtg tcacgtcatg agtgggtgtt tcgccaatcc atgaaacgca cctagatatc   1140
taaaacacat atcaattgcg aatctgcgaa gtgcgagcca ttaaccacgt aagcaaacaa   1200
acaatctaaa ccccaaaaaa aatctatgac tagccaatag caacctcaga gattgatatt   1260
tcaagataag acagtattta gatttctgta ttatatatag cgaaaatcgc atcaatac      1318

SEQ ID NO: 20             moltype = DNA  length = 1696
FEATURE                   Location/Qualifiers
source                    1..1696
                          mol_type = other DNA
                          organism = synthetic construct
SEQUENCE: 20
caaatttatt atgtgttttt tttccgtggt cgagattgtg tattattctt tagttattac     60
aagactttta gctaaaattt gaaagaattt actttaagaa atcttaaca tctgagataa    120
tttcagcaat agattatatt tttcattact ctagcagtat ttttgcagat caatcgcaac    180
atatggtt gttagaaaaa atgcactata tatatatat atgtgtgtgt gtatatggtc aaagaaattc  240
gcatgatata taatatatat atatatatat atgtgtgtgt gtatatggtc aaagaaattc    300
ttatacaaat atacacgaac acatatattt gacaaaatca agtattaca ctaaacaatg     360
agttggtgca tggccaaaac aaaatgtag attaaaaatt ccagcctcca aaaaaaaatc    420
caagtgttgt aaagcattat atatatatag tagatcccaa attttttgtac aattccacac   480
tgatcgaatt tttaaagttg aatatctgac gtaggatttt tttaatgtct tacctgacca    540
```

-continued

```
tttactaata acattcatac gttttcattt gaaatatcct ctataattat attgaatttg    600
gcacataata agaaacctaa ttggtgattt attttactag taaatttctg gtgatgggct    660
ttctactaga aagctctcgg aaaatcttgg accaaatcca tattccatga cttcgattgt    720
taaccctatt agttttcaca aacatactat caatatcatt gcaacggaaa aggtacaagt    780
aaaacattca atccgatagg gaagtgatgt aggaggttgg gaagacaggc ccagaaagag    840
atttatctga cttgttttgt gtatagtttt caatgttcat aaaggaagat ggagacttga    900
gaagtttttt ttggactttg tttagctttg ttgggcgttt ttttttttga tcaataactt    960
tgttgggctt atgatttgta atattttcgt ggactcttta gtttatttag acgtgctaac   1020
tttgttgggc ttatgacttg ttgtaacata ttgtaacaga tgacttgatg tgcgactaat   1080
ctttacacat taaacatagt tctgtttttt gaaagttctt attttcattt ttatttgaat   1140
gttatatatt tttctatatt tataattcta gtaaaaggca aattttgctt ttaaatgaaa   1200
aaaatatata ttccacagtt tcacctaatc ttatgcattt agcagtacaa attcaaaaat   1260
ttcccatttt tattcatgaa tcataccatt atatattaac taaatccaag gtaaaaaaaa   1320
ggtatgaaag ctctatagta agtaaaatat aaattcccca taaggaaagg gccaagtcca   1380
ccaggcaagt aaaatgagca agcaccactc caccatcaca caatttcact catagataac   1440
gataagattc atggaattat cttccacgtg gcattattcc agcggttcaa gccgataagg   1500
gtctcaacac ctctccttag gcctttgtgg ccgttaccaa gtaaaattaa cctcacacat   1560
atccacactc aaaatccaac ggtgtagatc ctagtccact tgaatctcat gtatcctaga   1620
ccctccgatc actccaaagc ttgttctcat tgttgttatc attatatata gatgaccaaa   1680
gcactagacc aaacct                                                   1696

SEQ ID NO: 21          moltype = DNA  length = 469
FEATURE                Location/Qualifiers
source                 1..469
                       mol_type = other DNA
                       organism = synthetic construct
SEQUENCE: 21
ggtactcctg agatactata ccctcctgtt ttaaaatagt tggcattatc gaattatcat     60
tttactttt aatgttttct cttcttttaa tatattttat gaattttaat gtattttaaa    120
atgttatgca gttcgctctg gacttttctg ctgcgcctaa cttgggtgt actgggccta    180
aattcagcct gaccgaccgc ctgcattgaa taatggatga gcaccggtaa aatccgcgta    240
cccaactttc gagaagaacc gagacgtggc gggccgggcc accgacgcac ggcaccagcg    300
actgcacacg tcccgccggc gtacgtgtac gtgctgttcc ctcactggcc gcccaatcca    360
ctcatgcatg cccacgtaca cccctgccgt ggcgcgccca gatcctaatc ctttcgccgt    420
tctgcacttc tgctgcctat aaatggcggc atcgaccgtc acctgcttc                469

SEQ ID NO: 22          moltype = DNA  length = 1099
FEATURE                Location/Qualifiers
source                 1..1099
                       mol_type = other DNA
                       organism = synthetic construct
SEQUENCE: 22
cagcggggca gcgcaacaca aaaggggggg aggatgccgg cgaccacgct agtgaccatg     60
aagcaagatg atgtgaaagg gaggaccgga cgagggttgg acctctgctg ccgacatgaa    120
gagcgtgatg tgtagaagga gatgttagac cagatgccga cgcaactagc cctggcaagg    180
tcacccgact gatatcgctg cttgcccttg tcctcatgta cacaatcagc ttgcttatct    240
ctcccatact ggtcgtttgt ttcccgtggc cgaaatagaa gaagacagag gtaggttttg    300
ttagagaatt ttagtggtat tgtagcctat ttgtaatttt gttgtacttt attgtattaa    360
tcaataaagg tgtttcattc tattttgact caatgttgaa tccattgatc tcttggtgtt    420
gcactcagta tgttagaata ttacattccg ttgaaacaat cttggttaag ggttggaaca    480
tttttatccg ttcgtgaaac atccgtaata ttttcgttga aacaattttt atcgacagca    540
ccgtccaaca atttacacca atttggacgt gtgatacata gcagtcccca agtgaaactg    600
accaccagtt gaaaggtata caaagtgaac ttattcatct aaaagaccgc agagatgggc    660
cgtgggccgt ggcctgcgaa acgcagcgtt caggcccatg agcatttatt ttttaaaaaa    720
atatttcaca acaaaaaaga gaacggataa aatccatcg aaaaaaaaaa ctttcctacg    780
catcctctcc tatctccatc cacggcgagc actcatccaa accgtccatc cacgcgcaca    840
gtacacacac atagttatcg tctctccccc cgatgagtca ccaccgtgt cttcgagaaa    900
cgcctcgccc gacaccgtac gtggcgccac cgccgcgcct gccgctgga cacgtccggc    960
tcctctccac gccgcgctgg ccaccgtcca ccggctcccg cacacgtctc cctgtctccc   1020
tccacccatg ccgtggcaat cgagctcatc tcctcgcctc ctccggctta taaatggcgg   1080
ccaccacctt cacctgctt                                                1099

SEQ ID NO: 23          moltype = DNA  length = 246
FEATURE                Location/Qualifiers
source                 1..246
                       mol_type = other DNA
                       organism = synthetic construct
SEQUENCE: 23
gtggcctggg aaaagagaga gcccaaccaa ggcggcccat ctgcgacgct tcggcactgt     60
caagcatccc gcacaggcgc agcaccgcag tcatcggtga catttgtcgc tacagctgtt    120
tcaggcatct gccacctcgg tcacatgccg tccgccacgt cgagaccgcg agctccctac    180
gtgtcacgcc cagccatgcc cgacgtctcc ggtgccgtgt tttaaagaac gcgccgtagc    240
gcactg                                                               246

SEQ ID NO: 24          moltype = DNA  length = 786
FEATURE                Location/Qualifiers
source                 1..786
                       mol_type = other DNA
                       organism = synthetic construct
```

```
SEQUENCE: 24
gacatggagg tggaaggcct gacgtagata gagaagatgc tcttagcttt cattgtcttt    60
cttttgtagt catctgattt acctctctcg tttatacaac tggttttta aacactcctt    120
aactttcaa attgtctctt tctttaccct agactagata atttaatgg tgattttgct    180
aatgtggcgc catgttagat agaggtaaaa tgaactagtt aaaagctcag agtgataaat    240
caggctctca aaaattcata aactgttttt taaatatcca aatattttta catgaaaat    300
aataaaattt agtttagtat taaaaaattc agttgaatat agttttgtct tcaaaaatta    360
tgaaactgat cttaattatt tttccttaaa accgtgctct atctttgatg tctagtttga    420
gacgattata taattttttt tgtgcttaac tacgacgagc tgaagtacgt agaaatacta    480
gtggagtcgt gccgcgtgtg cctgtagcca ctcgtacgct acagcccaag cgctagagcc    540
caagaggccg gaggtggaag gcgtcgcggc actatagcca ctcgccgcaa gagcccaaga    600
gaccggagct ggaaggatga gggtctgggt gttcacgaat tgcctggagg caggaggctc    660
gtcgtccgga gccacaggcg tggagacgtc cgggataagg tgagcagccg ctgcgatagg    720
ggcgcgtgtg aaccccgtcg cgccccacgg atggtataag aataaaggca ttccgcgtgc    780
aggatt                                                                786

SEQ ID NO: 25          moltype = DNA   length = 728
FEATURE                Location/Qualifiers
source                 1..728
                       mol_type = other DNA
                       organism = synthetic construct
SEQUENCE: 25
ctgcgtgtac aactaatata attgtccaaa caatttctgt ggcacgtact taagtttgag    60
ccaggataca aactttggcc gctaatggtt gctgtcgccg gtcaagaggg cgttggctac    120
ttgagttaga tttggttgt gtttcatccc cacgtacgtc cagcaaagaa aaattgaagc    180
tagtgcatgc atgttcgtc atcaaatgca tggccggccg gataccaatt tgaactgtag    240
ctatcgacgt acgcatgtat taatttatat cagagaagac aaggaacaca gatacataca    300
tgtcgaaaca atcatttcct atggcacttg agctagctag catacaattt tgtttaaat    360
gaaatgaaac tgaagacgat cgatcgaatt gaaggttgtg gttcgtgagc aatgcaatgc    420
agtttcacag aacgttgcca atgcaacaag ccaccaagaa aagagaagtc tactcgatct    480
tgcaatgatt aggcttggat gatgcgtggg gccacgtacg tatggacatc gaagaaccc    540
atcctcagcg tgtggcctga gggtgatggc aaagctgatc cacacattgc ggccccctt    600
ccccctcag agaccctgac ctcccgagca cagccagcca ccgcgcaacg ccggccacca    660
ccaccaccac cataccctgct agcgctagct ctctttattt aacgccgccg tgtgcgtgcc    720
tcgacgac                                                              728

SEQ ID NO: 26          moltype = DNA   length = 3912
FEATURE                Location/Qualifiers
source                 1..3912
                       mol_type = other DNA
                       organism = synthetic construct
SEQUENCE: 26
acaccaataa aaatacacag caataaaatc gctacgtata tatatatata atatgtatta     60
tctattacaa gatagtaata gagtatagca agttgtatca tctaacaaac tatgcgaata    120
aaatttgaac attgtgacat gtagatgtag tgtaatttag ctaagtgctt atcatcagta    180
acatagaccg acttaacttt ttacgaaaaa aaaaagtaa catagaccga aaaatgcat    240
atcgtaaatt taatggaaaa cacaatttac gataagtaaa aacaaaaag aaattacgat    300
aagtcgagaa aaatgcaaca aattgagata aagtattgat aaaaccatga aagtgtcggc    360
gtatgtaaat gcggtgatta atgtgatcat tagagcgtgt gtgttaaacg cggcggtttt    420
agtggagatt gatcagctga taacactctt accgggacga atcaattcc atattcatgg    480
cttgttaaaa cctaagacat acgcaatctc taatttgcta gtatagttag ttctatatta    540
tttttcgact aataatgtaa acatatgatt attaagtcgc aaaaagagtg cttaacaacc    600
aaaaagtgga ttaattaact tggtgggaaa agttacaaaa cctttaatga ttactctttg    660
taccaagaat agtggcgaag cactataaga gcagagaaaa gaagctcaat aatgtactaa    720
aagttgtaga tttacagc ttaaatacac caaaattaat agaaaagttg gtaatttttt    780
aattcatggc tactgattta gattttagaa aacaatagta gtatcattgt cacatcttaa    840
acacacaata ggtatgtttt aaatcaaagg ccgtagttaa tttgtcaaaa atgtatgcat    900
ttggtatttg gatgtctccg aaaggatgga tatatggact tgttagataa tttcatacct    960
cagtatcaat agtcatggag cccaaattgc tcaaaaacat attttaatt ccaagacttt    1020
gatgaagacg taataatgag tccaatgggc catcagatac aatgttcgga atttaacggg    1080
tttgttagtt ataagtattg ggcttgacct atctggttca atgatatgta ggaacaaccc    1140
aatttgcaaa gctttattaa agactctt agttgtcgtc aaggtttaac ttgtagtagt    1200
tggtaagaaa ttctacgtga aataggcaac attacaaaaa caaaaatcaa ttcgaaatta    1260
tacaaaacga aaccaagtag taaccaacta cactattatg acattaatga ttagacattc    1320
ccaaatcata caagttcctg tcatgaagga aacaatggtc cgtatttgca aacgattaca    1380
aaaattcaaa ccaaaaatga aaaacgagt taaattatt ggtttataaa aatagtaatg    1440
tcaacagaag actagattgg gaaacctgaa gcgaacagag cttttaaaaa cgagtttgaa    1500
cggctgggat catttggtac aatacccacc gtaagtttgt ttaccctagg gatgcaagcc    1560
aaaggcccaa atcagttact acttactgct acaaccatcg tctcagcttt ttgctctcagc    1620
ttttactaa tgaagcatac aatttcttgg gcatgtcaca tctcgacacg tgtccactat    1680
tctcttctct tattgctac tcgttcgtag gcttctgtta atagatgatc tctctataac    1740
tctaacagtc ttttctttct ctttatttcg ttttggtatt taagtttca aattgaaaat    1800
aataggagga aagtctagt ttaaatatt gtttttttac aagtgaacgt gaaccaattt    1860
acctcttttt ttttatatat cctatcggct aatctggtta gtatcggtag aaatgcaccg    1920
aggtgctaca gagattaatg ctagggatag tcagaccgct tgtatttctg actatcaagt    1980
aaatctacgc ccaactcaca tatttcccaa acaaatgtga tttttttttt tttttttttt    2040
tttttttttt tttgtaaca aatgtgattt tgttttcaag gaaaatagaa cttacgtttg    2100
ggaattcac ccttcactaa agcttcctc tgccattaga ccacaaaggc ttgggcaatt    2160
taccatttt gtaaaagtag aaaacaaaat gcctaaaatg ttcatacttc attacatcaa    2220
```

```
caaggttatg cccacgatat agaggcatgt aacatttata tatatagtgg aagaagccta 2280
cgagctttat taataagtat aaactctgat tattaggtaa ataaattact taaaacgatt 2340
actcaactga caaaaccgta gttgaataat aaggttacta tgaataccga ttgaatattg 2400
caaagccgga attgaaaaat atataacaga tcaaatgttc aagtgtggtc ataattctca 2460
cataggtcat atagctgaac ccatgcatct atttactagt ctatagaaag tactagagac 2520
gcatacagct gaacctactc tattcttttta ttaattttgg ttctcgtgga tacaaaattc 2580
ctccaacatt tattagaacg aataaaacca atatgatgat gattagttat tggtaaacat 2640
ataaacgttg agtaaacttc aaaatagatt gaagtactat taagacttgc attttttccc 2700
cttgggttat attcttgaat cgtttcgaag tattttaact ttcaagaata gaaggttcct 2760
caactataaa caattacatt atcaaaacc atttctatgt aaacaacata attttttgtat 2820
attttagtct tccccaaaag tttgaccgat agggcggttt agaccgtata gtacgactgt 2880
acaacaaaaa ggactctgga gacctaaaga tccaaaacta tgcaaaataa agatacggtc 2940
ggaccaattt aatctaacaa aaccaaatcc ttatactaaa ctattaccg atacattttcc 3000
ataacaca gtacacacaa ttaaatcaaa cattattgga agaacaagat agaataattgg 3060
cttaatctcg aacgattaga gttatcctag agcctcggag cttttgtcac atataatata 3120
aactatggta tatataaaca tgactctcat ttgtatttat cgcaaggtac aattccacca 3180
attttttttcg tcccactcat acagctttaa ttgtgaaatc aatccataaa aaaccaacat 3240
gtgacatggt ctctataact ataactataa aatcacatc aacataaaag 3300
aaaaccaatc atattggcta aaaaaaacta acggtcgaaa aacgtataac cacaaaacca 3360
aaccggtcca accggtgtcc ccaatcacta tcaaagcatt aactaacttt cacaaggaaa 3420
agcatagttc agtttctcta catcgcttcc catcctctta accctgttta ctcgaatcat 3480
ccaccgttgg atcaaacacg cgctacaaat ctagcgcggt accgaggttt ttacacagtg 3540
gaatattacc atgcattgga aagcggcgtc tacaacaaac ggcgggtcat gtcaccgtca 3600
aaatcaacct ttcttaattc ctaacgccgt tacttatctc cgtttactaa aaatgttaat 3660
gcgtgtgaga gtgaagatca tatactaatt agaagtggct aatgttttaa cgtgacatta 3720
ttatcatagt taatggttcg atcagagttt taagtagtaa atgatataag tgtgtgtata 3780
taattgcata catatatact ctcacactct gacagatttg tcgtggtctt agtattctct 3840
ttcatggcta gttatatagg gctctagtac attatctctc tctccccatt tctctgtctc 3900
tctcttcttt aa                                                    3912
```

```
SEQ ID NO: 27         moltype = DNA  length = 1718
FEATURE               Location/Qualifiers
source                1..1718
                      mol_type = other DNA
                      organism = synthetic construct
SEQUENCE: 27
atctctcctc tcctctcctc tcctcccgtt ggtgtgactg tagtagatcc tttgcccgtg  60
tcagaacaag ctgctcctcg gaccgggtaa tgttaaacat cggaggagcc tttgcctagg 120
atccgtaacg gggaggaaag agaaaaaaaa ctaaggatga ttatgatac cgtgtaataa 180
ctgctaacta cagttagccc atctcagcgg actctctgcc ctatattgta tgtcactttc 240
tattataaac tacactatac aacctatgat gtaaataat gttttgcacg ttcatatata 300
aatcagtcga agaaagggtg cctcactaca gggaatggtt tctattggac accttagcat 360
tcaatcagtc atgtcccccc ccccccccaa aaaaaaatg cacccatcca gtcgatttt 420
gtcatatttg aattcggtgg tgctccatgc acgcgtacct gctttgacca atttatacga 480
tcaatatata acttacgttc ttacggttct tagactttat gagactttgc aagtatgttt 540
ggatacaaat cacactaatg tgcatctttg taaactaaat tcttttgatt aaatttgtaa 600
ttttaaggtt taacctgttt ttgttgtgta gacgacgtta ggcaccgatc gtcgcttcgc 660
tatatatctt tgttgtagac gacgttagac tccctagatta aataagcgaa accgatcgt 720
cgcttcgcta tctttgttta tttgtttgtg gctgctctac gctgaagagc ccacaggcca 780
cagccccaca cgacacgtta ggcaccccca cccaccatcc gcgcataata taagctactg 840
caaaatatat gccggcggag cccgagcgag cttttgtactt gctccgccgt ggcctggctc 900
caggatgctt tggatttcgt gcggcgccgt acgtccaggc aaacagacaa gtggagctgc 960
atgtcctaaa agcccggcaa tcaaacacgc tctagcagca gcatggatca cagatatcag 1020
tcatggggtg gcgctggcgc gggtgggtgg ccaggtggag gtgggtgcat gtcgtcgtcg 1080
tcgtcccata cagaaattgg ctcacgtatg tatacgctgc gtacaggcag tagtacacaa 1140
ttactagcac caatgcaatc caacggatgg atcttcgcac acccgccacc cggttaaatt 1200
aagctactcc tacctctccc agtctccctt ggcctgcctc tatattttg ggcagcctcc 1260
accagccggg cggatggggt tggatcgtcg tatctgaggc ggcgtggtcg tccaggcgga 1320
aagcaacggc gcagggctgg gaccctagta ggtgcatgag gtcgtgcatg gcgcgcgagg 1380
tgcatggttt gggttaggcc taggaggttc tctctccatg gcatcgtgca ctcgcgccgc 1440
ttggctgccg ttctcgtgta tgcgcatgca ccaggcattt gcaccgcgcc gtgtatattt 1500
ctggcgtggg ggcggcgcc gcattggagc tgcagcccg tttcggcacg dacacggac 1560
acctcccgtt agggtaagcc cggggcagtg ggtaactgcc cagcgccact actccgaatt 1620
taccctcctt ttattttaa agcttgggag aggggagaat ggatggatgg atggatgtag 1680
acgcgtgaaa aagatgcgcg agaccggcag cgtgtgct                          1718
```

```
SEQ ID NO: 28         moltype = DNA  length = 1280
FEATURE               Location/Qualifiers
source                1..1280
                      mol_type = other DNA
                      organism = synthetic construct
SEQUENCE: 28
tccaccgatc atcacacaca gccagtagtg ggggtgggcc aagcaatcag gcacccggca  60
atgcgagctg atgcgtgatg atggtgctac caacaaactg actataaaat ttctgatttg 120
aaagggattg gcctcgatat tttattagct ccccggcttt tgtcacgaca cgttagcatg 180
cgtgccttct agaagctagt ccgggtatta ccgctagaaa gttccgaaa tgaagcattt 240
accacccgta aagctcattt ttctttatga tgagtagaca cggtaccaac attgaggacc 300
gattggttgg ctcccaaaat ctgccctgcc aaactagggc aagttcataa attttgacat 360
tcgcttggtt ggcaatcaat taaatcctat tctaaaattc ttgcctaggt tttgatataa 420
```

```
catgccctat attttggtct actcaaattt tggtatggta aattttgaac accaacaaat    480
caggctatta tttatcttat ctctttctca atttcattac acagcaaggc agtaattaaa    540
aggaccgtat atacaatgga tgtaagaata aaatgtataa gtagaaatat attggcatgc    600
ctcgtgctgg tgcatgtcga tatgctctca attagaagtt ggagacaggt tatgcttagg    660
atagtcccaa cctatgatat ctgtgtgtct atactgccac ataagtaaga catcacttta    720
gaaattacat tctacaacct ataatttctt agtgtggatc cttaattaat tcatcatctc    780
tcctctcaat tcctcatcaa ttatgaagac accatcttct tccaatgcaa atttaacact    840
gtctaggatc taggttcagg tgttgatact gggtcttgca tgagatccag tttcttgttc    900
ttccaattct ctctcattta atatataatc acataagcaa agatcctat gtagctgcac     960
aattaatgct atggaaacta tcctaatcgg agggttggga ctgctcctgc ctatggcggc   1020
ttattcccca tttgcctaac ctgaaaatcg aaagggagtg catgacaggg caaacactag   1080
tgttgcctgc atcaataatc gtccatgatt atatagaggt agcatgactt ttttaggcgt   1140
cgtgtcctaa tcaatcagaa aagaaagcca acctaatcgc tatgggccgc aaccaccgat   1200
gcgactatgc gagtatatgg aaaccgttgc tactccccca ctatatatcg tggagtctga   1260
tggcaatcca acggcagacg                                                1280

SEQ ID NO: 29          moltype = DNA   length = 51
FEATURE                Location/Qualifiers
source                 1..51
                       mol_type = other DNA
                       organism = synthetic construct
SEQUENCE: 29
tatatcatcg ttctctctat aaactttata gaactttgtt ctgattttct c              51

SEQ ID NO: 30          moltype = AA    length = 734
FEATURE                Location/Qualifiers
source                 1..734
                       mol_type = protein
                       organism = Arabidopsis thaliana
SEQUENCE: 30
MKGATLVALA ATIGNFLQGW DNATIAGAMV YINKDLNLPT SVQGLVVAMS LIGATVITTC     60
SGPISDWLGR RPMLILSSVM YFVCGLIMLW SPNVYVLCFA RLLNGFGAGL AVTLVPVYIS    120
ETAPPEIRGQ LNTLPQFLGS GGMFLSYCMV FTMSLSDSPS WRAMLGVLSI PSLLYLFLTV    180
FYLPESPRWL VSKGRMDEAK RVLQQLCGRE DVTDEMALLV EGLDIGGEKT MEDLLVTLED    240
HEGDDTLETV DEDGQIRLYG THENQSYLAR PVPEQNSSLG LRSRHGSLAN QSMILKDPLV    300
NLFGSLHEKM PEAGGNTRSG IFPHFGSMFS TTADAPHGKP AHWEKDIESH YNKDNDDYAT    360
DDGAGDDDDS DNDLRSPLMS RQTTSMDKDM IPHPTSGSTL SMRRHSTLMQ GNGESSMGIG    420
GGWHMGYRYE NDEYKRYYLK EDGAESRRGS IISIPGGPLW GGSYIHASAL VSRSVLGPKS    480
VHGSAMVPPE KIAASGPLWS ALLEPGVKRA LVVGVGIQIL QQFSGINGVL YYTPQILERA    540
GVDILLSSLG LSSISASFLI SGLTTLLMLP AIVVAMRLMD VSGRRSLLLW TIPVLIVSLV    600
VLVISELIHI SKVVNAALST GCVVLYFCFF VMGYGPFQTS SVLKSSQQAD RGLCIAICAM    660
VFWIGDIIVT YSLPVLLSSI ELVGVFSIYA AVCVISWIFV YMKVPETKGM PLEVITDYFA    720
FGAQAQASAP SKDI                                                      734

SEQ ID NO: 31          moltype = AA    length = 257
FEATURE                Location/Qualifiers
source                 1..257
                       mol_type = protein
                       organism = Glycine max
SEQUENCE: 31
MADSSREENV YMAKLAEQAE RYEEMVEFME KVAKTVEVEE LTVEERNLLS VAYKNVIGAR     60
RASWRIISSI EQKEESRGNE DHVAIIKEYR GKIEAELSKI CDGILNLLES NLIPSAASPE    120
SKVFYLKMKG DYHRYLAEFK TGAERKGAAE STLLAYKSAQ DIALADLAPT HPIRLGLALN    180
FSVFYYEILN SPDRACNLAK QAFDEAISEL DTLGEESYKD STLIMQLFRD NLTLWTSDIT    240
DDAGDEIKET FKQQPGE                                                   257

SEQ ID NO: 32          moltype = AA    length = 283
FEATURE                Location/Qualifiers
source                 1..283
                       mol_type = protein
                       organism = Arabidopsis thaliana
SEQUENCE: 32
MNGGEKLESI PIDLIIEIHS RLPAESVARF RCVSKLWGSM FRRPYFTELF LTRSRARPRL     60
LFVLQHNRKW SFSVFSSPQN QNIYEKPSFV VADFHMKFSV STFPDFHSCS GLIHFSMMKG    120
AYTVPVVCNP RTGQYAVLPK LTRTRYENSY SFVGYDPIEK QIKVLFMSDP DSGDDHRILT    180
LGTTEKMLGR KIECSLTHNI LSNEGVCING VLYYKASRIV ESSSDDDTSD DDDDDHERSD    240
VIVCFDFRCE KFEFIVICFY GQLINSVQLS LKQKSHQKLD LII                      283

SEQ ID NO: 33          moltype = AA    length = 240
FEATURE                Location/Qualifiers
source                 1..240
                       mol_type = protein
                       organism = Agrobacterium tumefaciens
SEQUENCE: 33
MDLRLIFGPT CTGKTSTAVA LAQQTGLPVL SLDRVQCCPQ LSTGSGRPTV EELKGTSRLY     60
LDDRPLVKGI IAAKQAHERL MGEVNYEAH GGLILEGGSI SLLKCMAQSS YWSADFRWHI    120
IRHELAHEET FMNVAKARVK QMLRPASGLS IIQELVDLWK EPRLRRILKE IDGYRYAMLF    180
VSQNQITSDM LLQLDADMED KLIHGIAQEY LIHARRQEQK FPRVNAAAYD GFEGHPFGMY    240
```

```
SEQ ID NO: 34              moltype = AA  length = 240
FEATURE                    Location/Qualifiers
source                     1..240
                           mol_type = protein
                           organism = Agrobacterium tumefaciens
SEQUENCE: 34
MDLRLIFGPT CTGKTSTAVA LAQQTGLPVL SLDRVQCCPQ LSTGSGRPTV EELKGTSRLY    60
LDDRPLVKGI IAAKQAHERL MGEVNYNYEAH GGLILEGGSI SLLKCMAQSS YWSADFRWHI  120
IRHELADEET FMNVAKARVK QMLRPAAGLS IIQELVDLWK EPRLRPILKE IDGYRYAMLF   180
ASQNQITSDM LLQLDADMED KLIHGIAQEY LIHARRQEQK FPRVNAAAYD GFEGHPFGMY   240

SEQ ID NO: 35              moltype = AA  length = 624
FEATURE                    Location/Qualifiers
source                     1..624
                           mol_type = protein
                           organism = Zea mays
SEQUENCE: 35
MASSLLSSPA KPTITTTTKT TPAPRPARSA HVHVLSAARC LRLRLRASSQ HPPPPPTPRS    60
RRPEYVPNRI DDPNYVRIFD TTLRDGEQSP GATMTSAQKL VVARQLARLG VDIIEAGFPA   120
SSPDDLDAVR SIAIEVGNPA PAGEDAAVHV PVICGLSRCN RRDIDAAWEA VRHARRPRIH   180
TFIATSDIHM QHKLRKTPDQ VVAIAREMVA YARSLGCTDV EFSPEDAGRS NREFLYHILG   240
EVIKAGATTL NIPDTVGYNL PYEFGKLIAD IKANTPGIEK AIISTHCQND LGLATANTLA   300
GARAGARQLE VTINGIGERA GNASLEEVVM AIKCRRELLD GLYTGIDSRH ITLTSKMVQE   360
HSGLHVQPHK AIVGANAFAH ESGIHQDGML KYKGTYEIIS PDDIGLTRAN EFGIVLGKLS   420
GRHAVRSKLV ELGYEIGDKE FEDFFKRYKE VAEKKKRVTD EDLEALLSDE IFQPKVIWSL   480
ADVQATCGTL ALSTATVKLI APDGEEKIAC SVGTGPVDAA YKAVDKIIQI PTVLREYSMT   540
SVTEGIDAIA TTRVVVTGDV SNNAKHALTG QSFNRSFSGS GASMDIVVSS VRAYLSALNK   600
ICSFAGAVKA SSDVAETASV PSTE                                          624

SEQ ID NO: 36              moltype = AA  length = 240
FEATURE                    Location/Qualifiers
source                     1..240
                           mol_type = protein
                           organism = Agrobacterium tumefaciens
SEQUENCE: 36
MDLRLIFGPT CTGKTSTAVA LAQQTGLPVL SLDRVQCCPQ LSTGSGRPTV EELKGTSRLY    60
LDDRPLVKGI IAAKQAHERL MGEVNYNYEAH GGLILEGGSI SLLKCMAQSS YWSADFRWDI  120
IRHELADEET FMNVAKARVK QMLRPAAGLS IIQELVDLWK EPRLRPILKE IDGYRYAMLF   180
ASQNQITSDM LLQLDADMED KLIHGIAQEY LIHARRQEQK FPRVNAAAYD GFEGHPFGMY   240

SEQ ID NO: 37              moltype = AA  length = 257
FEATURE                    Location/Qualifiers
source                     1..257
                           mol_type = protein
                           organism = Glycine max
SEQUENCE: 37
MSDSSREENV YMAKLAEQAE RYEEMVEFME KVAKTVEVEE LTVEERNLLS VAYKNVIGAR    60
RASWRIISSI EQKEESRGNE DHVAIIKEYR GKIEAELSKI CDGILNLLES NLIPSAASPE   120
SKVFYLKMKG DYHRYLAEFK TGAERKEAAE STLLAYKSAQ DIALADLAPT HPIRLGLALN   180
FSVFYYEILN SPDRACNLAK QAFDEAISEL DTLGEESYKD STLIMQLFRD NLTLWTSDIT   240
DDAGDEIKET FKRQPGE                                                  257

SEQ ID NO: 38              moltype = AA  length = 734
FEATURE                    Location/Qualifiers
source                     1..734
                           mol_type = protein
                           organism = Arabidopsis thaliana
SEQUENCE: 38
MKGATLVALA ATIGNFLQGW DNATIAGAMV YINKDLNLPT SVQGLVVAMS LIGATVITTC    60
SGPISDWLGR RPMLILSVM YFVCGLIMLW SPNVYVLCFA RLLNGFGAGL AVTLVPVYIS   120
ETAPPEIRGQ LNTLPQFLGS GGMFLSYCMV FTMSLSDSPS WRAMLGVLSI PSLLYLFLTV   180
FYLPESPRWL VSKGRMDEAK RVLQQLCGRE DVTGKMALLV EGLDIGGEKT MEDLLVTLED   240
HEGDDTLETV DEDGQMRLYG THENQSYLAR PVPEQNSSLG LRSRHGSLAN QSMILKDPLV   300
NLFGSLHEKM PEAGGNTRSG IFPHFGSMFS TTADAPHGKP AHWEKDIESH YNKDNDDYAT   360
DDGAGDDDDS DNDLRSPLMS RQTTSMDKDM IPHPTSGSTL SMRRHSTLMQ GNGESSMGIG   420
GGWHMGYRYE NDEYKRYYLK EDGAESRRGS IISIPGGPDG GGSYIHASAL VSRSVLGPKS   480
VHGSAMVPPE KIAASGPLWS ALLEPGVKRA LVVGVGIQIL QQFSGINGVL YYTPQILERA   540
GVDILLSSLG LSSISASFLI SGLTTLLMLP AIVVAMRLMD VSGRRSLLLW TIPVLIVSLV   600
VLVISELIHI SKVVNAALST GCVVLYFCFF VMGYGPIPNI LCSEIFPTRV RGLCIAICAM   660
VFWIGDIIVT YSLPVLLSSI GLVGVFSIYA AVCVISWIFV YMKVPETKGM PLEVITDYFA   720
FGAQAQASAP SKDI                                                     734

SEQ ID NO: 39              moltype = AA  length = 257
FEATURE                    Location/Qualifiers
source                     1..257
                           mol_type = protein
                           organism = Glycine max
SEQUENCE: 39
MSDSSREENV YMAKLADEAE RYEEMVEFME KVAKTVEVEE LTVEERNLLS VAYKNVIGAR    60
```

-continued

```
RASWRIISSI EQKEESRGNE DHVAIIKEYR GKIEAELSKI CDGILNLLES NLIPSAASPE    120
SKVFYLKMKG DYHRYLAEFK TGAERKEAAE STLLAYKSAQ DIALADLAPT HPIRLGLALN    180
FSVFYYEILN SPDRACNLAK QAFDEAISEL DTLGEESYKD STLIMQLLRD NLTLWTSDIT    240
DIAGDEIKET SKQQPGE                                                  257
```